(12) United States Patent
Yue

(10) Patent No.: US 10,821,306 B2
(45) Date of Patent: Nov. 3, 2020

(54) MRI-CT COMPATIBLE DYNAMIC MOTION PHANTOM

(71) Applicant: THE TRUSTEES OF INDIANA UNIVERSITY, Indianapolis, IN (US)

(72) Inventor: Yong Yue, Los Angeles, CA (US)

(73) Assignee: The Trustees of Indiana University, Bloomington, IN (US)

( * ) Notice: Subject to any disclaimer, the term of this patent is extended or adjusted under 35 U.S.C. 154(b) by 45 days.

(21) Appl. No.: 15/746,750

(22) PCT Filed: Jul. 27, 2016

(86) PCT No.: PCT/US2016/044338
§ 371 (c)(1),
(2) Date: Jan. 22, 2018

(87) PCT Pub. No.: WO2017/019809
PCT Pub. Date: Feb. 2, 2017

(65) Prior Publication Data
US 2018/0161599 A1 Jun. 14, 2018

Related U.S. Application Data

(60) Provisional application No. 62/197,740, filed on Jul. 28, 2015.

(51) Int. Cl.
*A61N 5/01* (2006.01)
*A61N 5/10* (2006.01)
(Continued)

(52) U.S. Cl.
CPC ............ *A61N 5/1075* (2013.01); *A61B 6/583* (2013.01); *A61N 5/107* (2013.01); *A61N 5/1039* (2013.01);
(Continued)

(58) Field of Classification Search
CPC .. A61B 6/00; A61B 6/10; A61B 6/582; A61B 6/583; A61B 6/584; A61B 6/585;
(Continued)

(56) References Cited

U.S. PATENT DOCUMENTS 5,071,602 A 12/1991 Nambu et al.
6,843,145 B2 1/2005 Jaszczak et al.
(Continued)

FOREIGN PATENT DOCUMENTS

JP 1989086953 A 3/1989
JP 1995080089 B2 3/1995
(Continued)

OTHER PUBLICATIONS

Chamberland "Application of three-dimensional motion tracking of low-activity fiducial position-emitting markers in radiation therapy and positron emission tomography", IEEE Nuclear Science Symposium & Medical Imaging (Year: 2014).*
(Continued)

*Primary Examiner* — David P Porta
*Assistant Examiner* — Mamadou Faye

(57) ABSTRACT

MRI for radiotherapy simulation, planning and/or treatment guidance requires accurate motion assessment and real-time tumor monitoring. Clinical image-guided radiotherapy requires precise quality assurance of targeted tumor geometry and motion phase and amplitudes for both MRI and CT images. In various embodiments, the MRI-CT compatible phantom described herein is designed to validate the accuracy and performance of clinical procedures in both a 4D MRI sequence and 4D CT imaging, and to provide equivalent dynamic image contrast and quality for both imaging modalities. Additionally described is a PET compatible phantom.

20 Claims, 11 Drawing Sheets

(51) Int. Cl.
*G09B 23/30* (2006.01)
*G01R 33/58* (2006.01)
*A61B 6/00* (2006.01)
*G01R 33/48* (2006.01)
*A61B 34/10* (2016.01)
*A61B 34/20* (2016.01)

(52) U.S. Cl.
CPC .......... *G01R 33/58* (2013.01); *G09B 23/303* (2013.01); *A61B 34/10* (2016.02); *A61B 34/20* (2016.02); *A61N 2005/1055* (2013.01); *A61N 2005/1076* (2013.01); *G01R 33/4812* (2013.01)

(58) Field of Classification Search
CPC ...... A61B 6/586; A61B 6/587; A61N 5/1049; A61N 5/1064; A61N 5/1067; A61N 5/1069; A61N 5/107; A61N 5/1071; A61N 5/1075; A61N 2005/105; A61N 2005/1051; A61N 2005/1052; A61N 2005/1054; A61N 2005/1055; A61N 2005/1056; G01D 18/002; G01D 18/004; G01D 18/006; G01N 2223/3035; G01N 2223/3032; G01N 2223/3037; G09B 23/28; G09B 23/286; G09B 23/30
See application file for complete search history.

(56) References Cited

U.S. PATENT DOCUMENTS

| | | | |
|---|---|---|---|
| 8,275,443 B2 | 9/2012 | Goldenberg et al. | |
| 2002/0102214 A1* | 8/2002 | Briley-Saebo | A61K 49/128 424/9.36 |
| 2002/0178845 A1 | 12/2002 | Jaszczak et al. | |
| 2004/0005035 A1 | 1/2004 | White et al. | |
| 2009/0110140 A1* | 4/2009 | Krautim | A61N 5/1048 378/18 |
| 2009/0326364 A1 | 12/2009 | Goldenberg et al. | |
| 2010/0167251 A1* | 7/2010 | Boutchko | A61B 5/416 434/267 |
| 2011/0044524 A1 | 2/2011 | Wang et al. | |
| 2012/0319685 A1* | 12/2012 | Burger | G01R 33/5676 324/309 |
| 2013/0292580 A1* | 11/2013 | Schubert | A61N 5/1048 250/395 |
| 2014/0163375 A1* | 6/2014 | Wasielewski | A61B 8/4494 600/443 |
| 2015/0306340 A1* | 10/2015 | Giap | G16H 40/63 600/301 |
| 2017/0169734 A1* | 6/2017 | Wen | G09B 23/32 |

FOREIGN PATENT DOCUMENTS

| | | |
|---|---|---|
| JP | 2001500501 A | 1/2001 |
| JP | 2003536107 A | 12/2003 |
| JP | 2012055549 A | 3/2012 |
| JP | 2018-521782 A1 | 8/2018 |
| WO | 1998010797 A2 | 3/1998 |
| WO | 2012032810 A1 | 3/2012 |
| WO | 2017019809 A1 | 2/2017 |

OTHER PUBLICATIONS

ISR and WO for PCT/US2016/044338 dated Oct. 7, 2016 (6 pages).
IPRP for PCT/US2016/044338 dated Feb. 8, 2018 (5 pages).

* cited by examiner

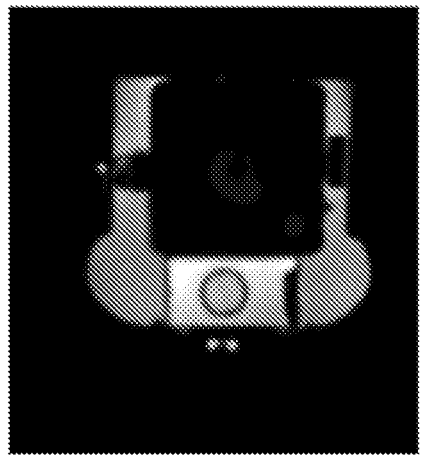
FIG. 3A
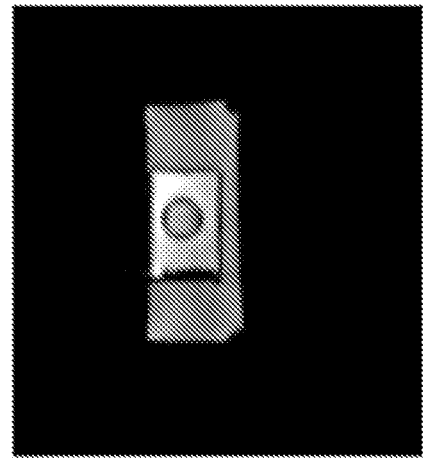
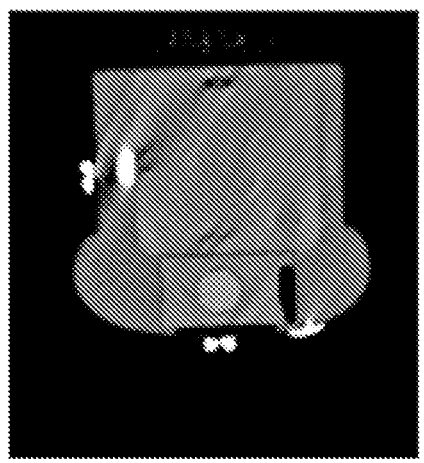
FIG. 3B
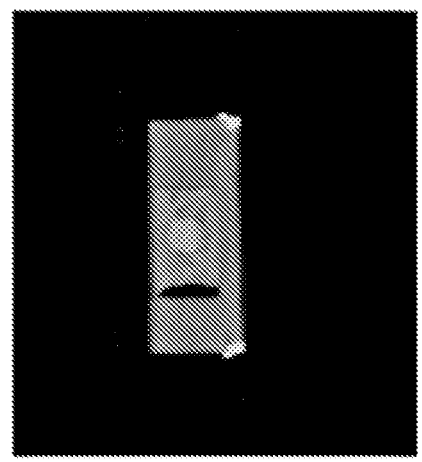
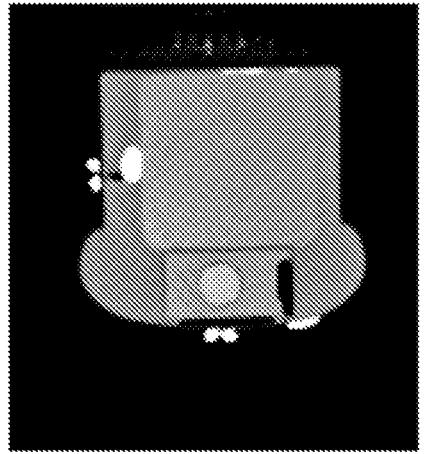
FIG. 3C
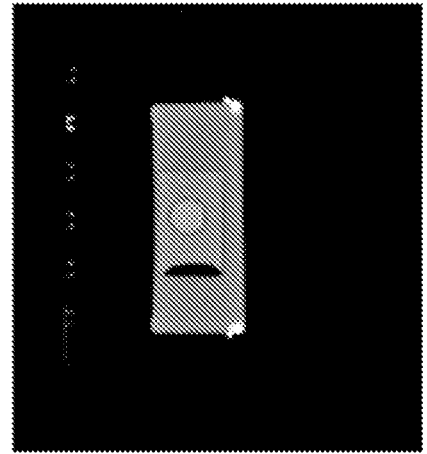

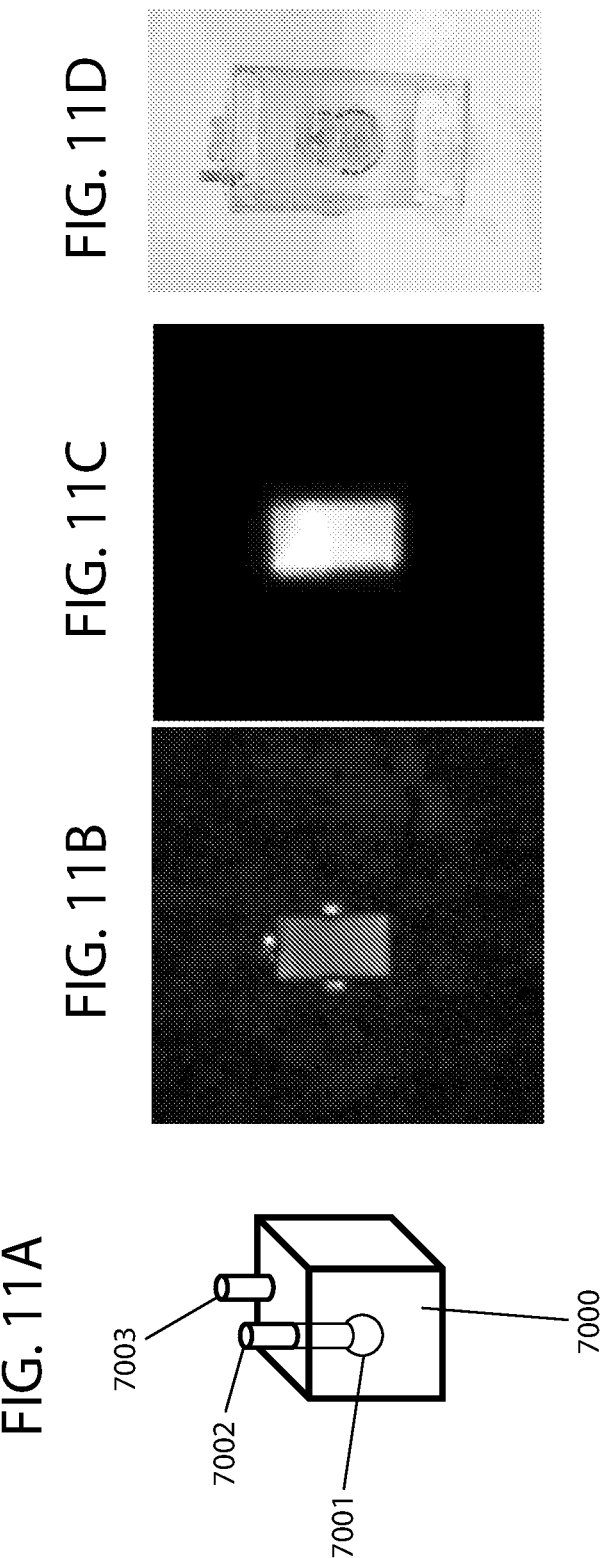

MRI-CT COMPATIBLE DYNAMIC MOTION PHANTOM

CROSS-REFERENCE TO RELATED APPLICATIONS

This application is a National Phase of International Application No. PCT/US2016/044338, filed Jul. 27, 2016, which designated the U.S. and that International Application was published under PCT Article 21(2) in English. This application claims benefit under 35 U.S.C. § 119(e) of U.S. Provisional Application No. 62/197,740, filed Jul. 28, 2015, the content of which is incorporated herein by reference in its entirety.

FIELD OF THE INVENTION

The present invention generally relates to the field of imaging.

BACKGROUND

The following description includes information that may be useful in understanding the present invention. It is not an admission that any of the information provided herein is prior art or relevant to the presently claimed invention.

With the recent development of MRI-Linacs and other MRI-based therapy systems, MRI-based methods for in-treatment room monitoring are going to be very important. Concurrently, intensive efforts are also being devoted to using MRI as the primary simulation and planning imaging modality for radiotherapy in a number of clinical sites. In any scenario utilizing MRI for simulation, planning and/or treatment guidance, accurate spatial-temporal resolved MRI would be an essential component of motion management in the clinical use of MRI-guided or monitored radiotherapy.

With the foregoing background in mind, there is a need in the art for an MRI-CT compatible system, which can be utilized to validate the imaging sequence of dynamic MRI and CT imaging and to provide quality assurance for MRI-guided radiotherapy.

SUMMARY

In various embodiments, the invention teaches a system that includes (1) a phantom, including a target that includes a first gel with a first concentration of gadolinium (Gd); a target container containing a second gel with a second concentration of Gd that is lower than the first concentration of Gd; and a water container containing water with a Gd concentration of $5 \times 10^{-6}$ Mol/mL-$5 \times 10^{-5}$ Mol/mL; wherein the target is embedded within the target container and stabilized with the second gel, and the target container is contained within the water container; (2) a collapsible air container operably connected to the phantom, such that inflation of the collapsible air container causes the phantom to move; (3) an air pump in fluid communication with the collapsible air container; and (4) an electronic controller, wherein the electronic controller is configured to modulate an air pressure generated by the air pump which in turn modulates the position of the phantom. In some embodiments, the air pump is positioned in a separate room from the phantom. In certain embodiments, the target is spherical. In some embodiments, the electronic controller includes a controller module configured to allow the system to mimic human respiratory motion. In some embodiments, the system is configured to simulate respiratory rates of 2-20 seconds per cycle and breathing depths of 3-30 mm. In some embodiments, the system further includes an air intake port, wherein the air intake port is connected to and in fluid communication with the collapsible air container. In certain embodiments, the air intake port includes an air intake valve, and the air intake valve is a one-way valve that only allows air to flow into the collapsible air container. In some embodiments, the system further includes a hose, wherein a first end of the hose connects to the air intake port and the second end of the hose connects to the air pump. In some embodiments, the system includes a linear actuator attached to an external surrogate, wherein the external surrogate comprises one or more markers, and wherein the linear actuator is attached to the phantom. In some embodiments, one or more of the markers are infrared markers. In certain embodiments, the external surrogate is an RPM box. In some embodiments, the linear actuator is in electronic communication with the electronic controller, and the electronic controller is configured to control the motion of the linear actuator. In some embodiments, the electronic controller is an RSD controller. In some embodiments, the system further includes a platform upon which the phantom rests. In some embodiments, the platform includes one or more wheels configured to allow the platform to roll. In some embodiments, the system further includes a bed upon which the one or more wheels of the platform rest. In some embodiments, the system further includes one or more tracks configured to accommodate the one or more wheels of the platform. In some embodiments, the system further includes a magnetic resonance imaging scanner. In some embodiments, the system further includes a computed tomography (CT) scanner. In some embodiments, the collapsible air container is a bellow.

In various embodiments, the invention teaches a kit that includes any of the systems described above and instructions for the use thereof for imaging the phantom with a CT scanner and/or an MRI scanner.

BRIEF DESCRIPTION OF THE DRAWINGS

Exemplary embodiments are illustrated in the referenced figures. It is intended that the embodiments and figures disclosed herein are to be considered illustrative rather than restrictive.

FIG. 3 depicts, in accordance with an embodiment of the invention, phantom images in axial (top) and coronal (bottom) views. (A) Static 3D-CT image, compared with phase resolved (B) 4D-CT image, and (C) 4D-MRI image.

FIGS. 11A-11D depict systems in accordance with various embodiments of the invention. FIG. 11A depicts components of a phantom configured for a PET or MRI scan. The components are described in the description of FIG. 10 above. FIG. 11B depicts an MRI image of the components depicted in FIG. 11A (container 7001 includes a composition with a relatively high concentration of Gd, compared to the concentration of Gd in the composition included in container 7000). FIG. 11C depicts a PET image of the components described in FIG. 11A (container 7001 includes a composition with a higher Curie value than the composition included in container 7000). FIG. 11D is a photograph of the components described in FIG. 11A.

DESCRIPTION OF THE INVENTION

Figure 1:
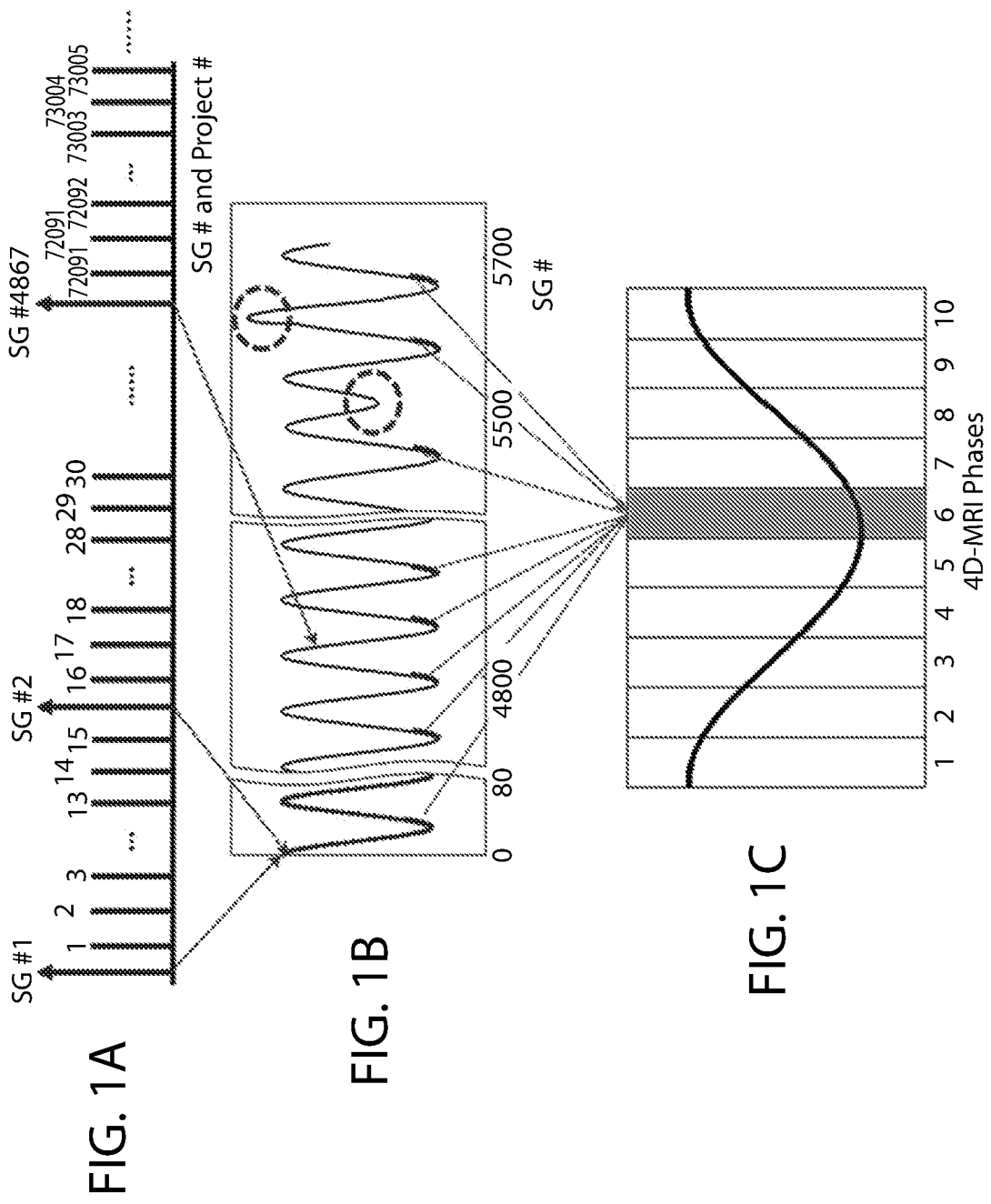
FIG. 1 depicts, in accordance with an embodiment of the invention, a flow chart for 4D-MRI acquisition and phase sorting of reconstruction. (A) Image sequence with k-space segments, consisting of self-gating (SG) and 15 radial projection lines, giving a temporal interval of ~98 ms between each SG line. A total of 86160 projections were collected with 5744 SG lines after an approximately 8 minute scan. (B) The superior-inferior (SI) respiratory curve is extracted by the PCA-based method. As shown in the left side curve, each point (in red) represents a SG line (indicated by arrows). Many SG lines contribute one cycle of the respiratory curve. The resultant curve represents the respiratory motion through the entire imaging acquisition. (C) The respiratory cycle is divided into 10 phases. The projections with the same phase number (shown in blue segments) are assigned to a resolved phase in the 4D (shown in blue shade). Furthermore, motion artifact removal is built in to the reconstruction. Any abnormal segments (shown in circled segments in (B)) will be excluded from reconstruction.

All references cited herein are incorporated by reference in their entirety as though fully set forth. Unless defined otherwise, technical and scientific terms used herein have the same meaning as commonly understood by one of ordinary skill in the art to which this invention belongs.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described.

By way of additional background, MRI is increasingly being used for radiotherapy planning, simulation, and in-treatment-room motion monitoring. To provide more detailed temporal and spatial MR data for these tasks, a novel self-gated MRI technique was developed with the advantage of k-space phase sorting, high isotropic spatial resolution, and high temporal resolution.

As represented by various embodiments of the invention, an MRI-CT compatible phantom was designed to validate the performance of the 4D-MRI sequence and 4D-CT imaging. In addition, various embodiments described herein are configured for positron emission tomography (PET) scans.

In some embodiments, a spherical target (diameter 23 mm, volume 6.37 ml) filled with high-concentration gadolinium (Gd) gel is embedded into a plastic box (35×40×63 mm$^3$) and stabilized with low-concentration Gd gel. The phantom, driven by an air pump, is able to produce human-type breathing patterns between 4 to 30 respiratory cycles per minute. In certain embodiments, 4D-CT of the phantom is acquired in cine mode, and reconstructed into 10 phases with slice thickness 1.25 mm. The 4D images sets can be imported into a treatment planning software for target contouring. The geometrical accuracy of the 4D MRI and CT images can be quantified using target volume, flattening and eccentricity. The target motion can be measured by tracking the centroids of the spheres in each individual phase.

As demonstrated in the experiments reported in the "Examples" section herein, motion ground-truth was obtained from input signals and real-time video recordings. The dynamic phantom described in the experiments of the "Examples" section has been operated in four respiratory rate (RR) settings, 6, 10, 15 and 20 per min, and was scanned with 4D-MRI and 4D-CT. 4D-CT images had target stretching, partial-missing and other motion artifacts in various phases, whereas the 4D-MRI images were visually free of those artifacts. Volume percentage difference for the 6.37 ml target ranged from 5.3±4.3% to 10.3±5.9% for 4D-CT, and 1.47±0.52 to 2.12±1.60 for 4D-MRI. With an increase of respiratory rate, the target volumetric and geometric deviations increase for 4D-CT images while remaining stable for the 4D-MRI images. Target motion amplitude errors at different RRs were measured with a range of 0.66-1.25 mm for 4D-CT and 0.2-0.42 mm for 4D-MRI. The results of Mann-Whitney tests indicated that 4D-MRI significantly outperforms 4D-CT in phase based target volumetric ($p=0.027$) and geometric ($p<0.001$) measures. Both modalities achieve equivalent accuracy in measuring motion amplitude ($p=0.828$).

As demonstrated in the experiments reported in the "Examples" section herein, the k-space self-gated 4D-MRI technique that was tested provides a robust method for accurately imaging phase-based target motion and geometry. Compared to 4D-CT, the current 4D-MRI technique demonstrates superior spatiotemporal resolution, and robust resistance to motion artifacts caused by fast target motion and irregular breathing patterns. The technique can be used extensively in abdominal targeting, motion gating, and toward implementing MRI-based adaptive radiotherapy.

As demonstrated in the experiments reported in the "Examples" section herein, a water-gel mixture was used to provide a typical background soft-tissue signal for both CT and MRI. To produce contrast in the target, high concentration gadolinium (Gd) was diluted in the target sphere, in order to create better SNR for both CT and MR. The plastic outside of the target was used to ensure a clearly defined boundary for both CT and MRI. These design decisions were successful at minimizing the image quality differences between the two image modalities.

Figure 8:
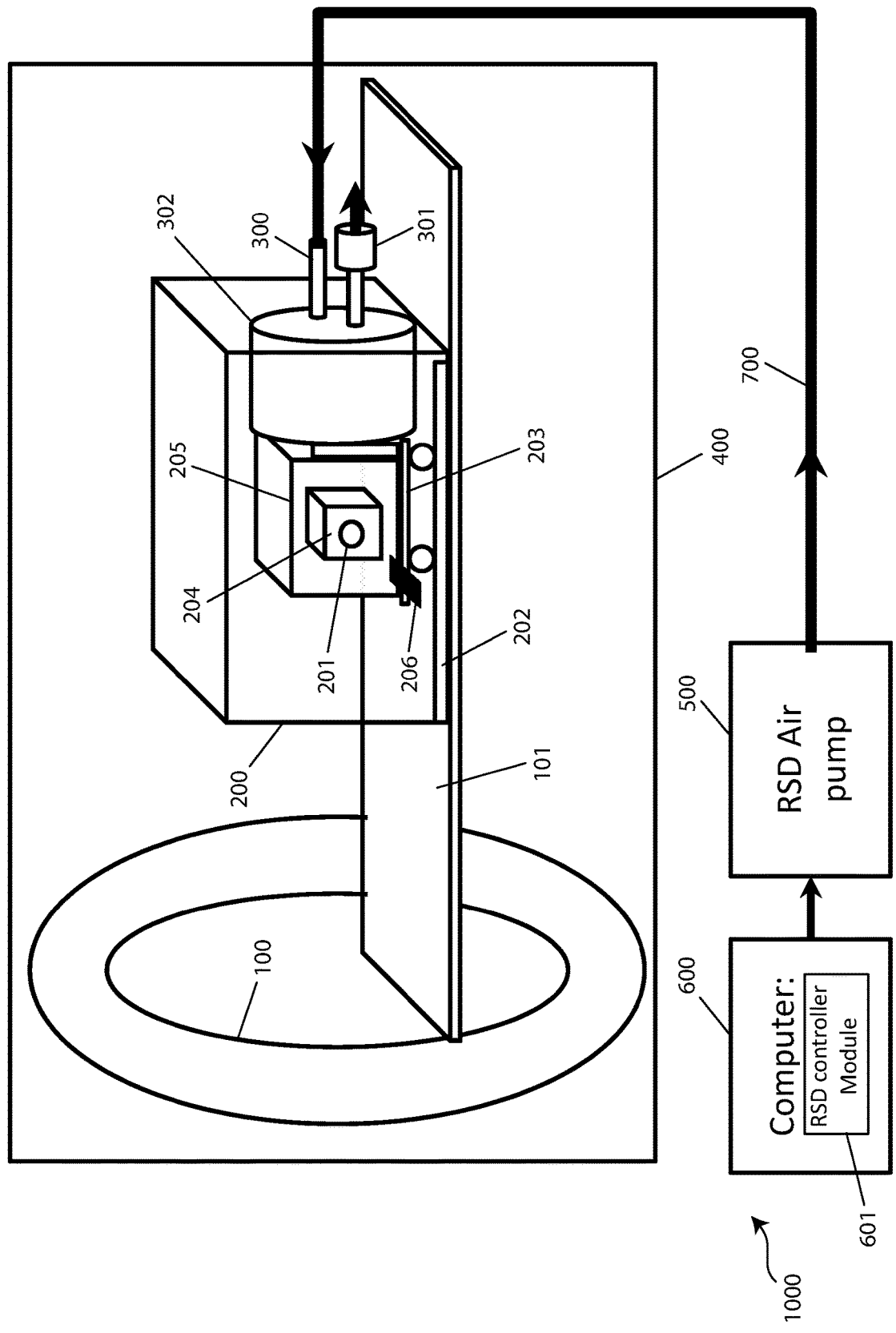
FIG. 8 depicts, in accordance with an embodiment of the invention, a system 1000 with a phantom setup that can be used for MRI imaging. The components of phantom 200 include: 1) Targets: Target 1 201 sealed with high concentration Gd-gel, is embedded in Target 2 204 sealed with low concentration Gd gel, whereas Target 2 is embedded in a water box 205 filled with weak concentration Gd water. 2) Motion components: a. Air Bellow 302 is driven by input air applied through input valve 300, and its output is controlled by adjustable valve 301, b. Plastic Rail Carrier 203 is used to connect the water box 205 and air bellow 302, and its traveling distance is monitored by a motion marker 206 and a ruler 202. 3) Air input is generated by the RSD air pump 500, which is controlled by the RSD controller module 601 through a computer 600. The air pump 500 and computer 600 are placed outside MRI scanner room 400, and connected to the phantom 200 through silicon air hose 700. All components inside MRI-room 400 are MRI-compatible.

As demonstrated in the experiments reported in the "Examples" section herein, in various embodiments the phantom can produce dynamic motion driven by an air pump which is placed outside the MRI room (FIG. 8). As shown in the experiments reported herein, human respiratory motion can be mimicked using the RSD controller module, which has the capability to produce various human respiratory rates (2-20 s/cycle) and breathing depths (3-30 mm). In some embodiments, the RSD controller model is able to provide two respiratory signals: pressured air generated by the air pump and mechanical motion generated by the linear actuator. The former is used to drive the phantom in the superior-inferior SI direction during both CT and MRI scans, and the latter output is used to drive the motion surrogate in the anterior-posterior (AP) direction for 4D-CT scans.

With the foregoing background in mind, in various embodiments the invention teaches a system that includes (1) a phantom that includes a target comprising a first gel with a first concentration of gadolinium (Gd); a target container containing a second gel with a second concentration of Gd that is lower than the first concentration of Gd; and a water container containing water; wherein the target is embedded within the target container and stabilized with the second gel, and the target container is contained within the water container; (2) a collapsible air container operably connected to the phantom, such that inflation of the collapsible air container causes the phantom to move; (3) an air pump in fluid communication with the collapsible air container; and (4) an electronic controller, wherein the electronic controller is configured to modulate an air pressure generated by the air pump which in turn modulates the position of the phantom. In some embodiments, the gel that includes a higher concentration of Gd includes Gd at a concentration ranging from $5\times10^{-3}$ Mol/mL to 0.25 Mol/mL. In some embodiments, the gel containing a lower concentration Gd includes Gd at a concentration ranging from $5\times10^{-4}$ Mol/mL to $5\times10^{-3}$ Mol/mL. In some embodiments, the water contained in the water container further contains Gd at a concentration of $5\times10^{-6}$ Mol/mL-$5\times10^{-5}$ Mol/mL. In some embodiments, the system further includes a linear actuator. In some embodiments, the system further includes an external surrogate mechanically connected to the linear actuator. In some embodiments, in addition to modulating air pressure, the computer-operated controller module is also configured to modulate the position of the external surrogate via the linear actuator (e.g. move it up and down).

Non-limiting examples of options of Gd chelated contrast agents that can be incorporated into the Gd-containing gels include gadoterate, gadodiamide, gadobenate, gadopentetate, gadoteridol, gadofosveset, gadoversetamide, gadoxetate, gadobutro, and combinations thereof. In some embodiments, the higher concentration Gd gel and the lower concentration Gd gel include the same agent (e.g. any of the Gd containing agents described above). In some embodiments, the containers housing the higher concentration Gd gel and/or the lower concentration Gd gel are clear (e.g. plastic). In some embodiments, one or more of the containers comprise, consists of, or consist essentially of polystyrene. In some embodiments, the container containing water (or weak concentration Gd water as described above) is comprised of a clear material (e.g. plastic), and is either partially or completely clear. In some embodiments, the container comprises, consists of, or consists essentially of polystyrene.

Figure 9:
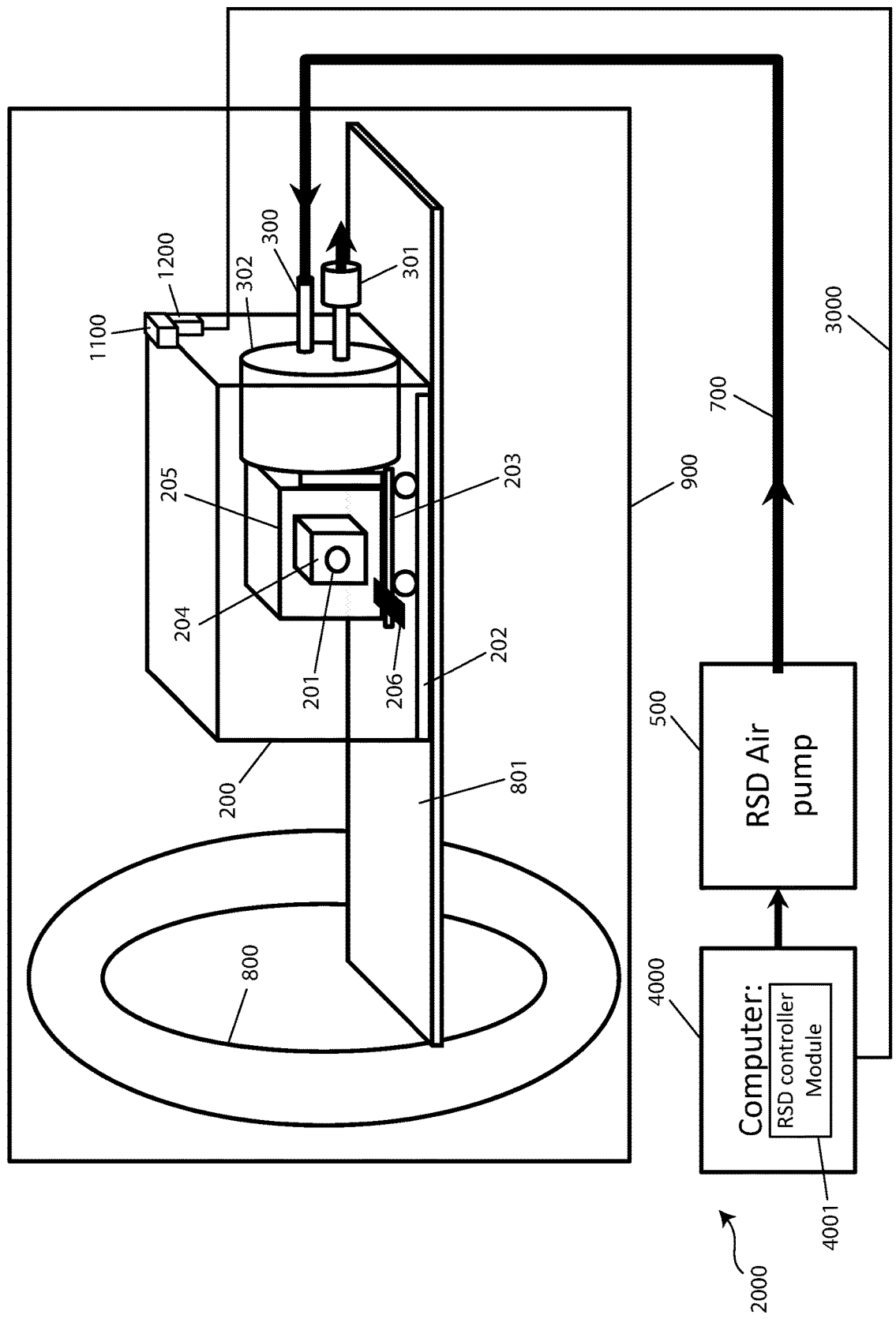
FIG. 9 depicts, in accordance with an embodiment of the invention, a phantom setup that can be used for CT imaging. In addition to most of the components of the MRI imaging setup depicted in FIG. 8, an infrared box (RPM box) 1100 is attached to a linear actuator 1200, which is attached to the outside wall of phantom container 200. The motion of the RPM box 1100, driven by the RSD controller module 4001, is used as a surrogate motion signal for 4D-CT image reconstruction. The control system is placed outside CT scanner room 900, and the MRI scanner of FIG. 8 is replaced with a CT machine 800.

In some embodiments, the air pump is positioned in a separate room from the phantom, for example as shown in FIGS. 8 and 9. In some embodiments, the target is spherical, but one of skill in the art would readily appreciate that the target could be of any suitable shape. In certain embodiments, the computer-operated controller module is configured to allow the system to mimic human respiratory motion. In certain embodiments, the system is configured to simulate respiratory rates of 2-20 seconds per cycle and breathing depths of 3-30 mm. In some embodiments, the simulated respiratory rates are controlled by using the computer and RSD control module to regulate the activity of the air pump and/or linear actuator, which in turn modulate the position of the target and phantom, as described in greater detail bellow. In some embodiments, the target simulates diaphragm motion and the external surrogate simulates chest wall motion. In various embodiments, the external surrogate is an RPM box, which is a marker block used in a Real-Time Position Management (RPM) system (Varian, CA). In various embodiments, the RPM box is a plastic (e.g. polystyrene) container labeled with two infrared reflective painted markers, which is designed to provide a visualized motion signal for an infrared camera in the RPM system. In some embodiments, the infrared camera is included in the systems used in conjunction with MRI, CT, and PET described herein. In some embodiments, the RPM box is placed on the tip of the linear actuator, which is configured to modulate the position of the RPM box (e.g., move it up and down). In some embodiments, the infrared camera is positioned in any place where it can view the RPM box. In some embodiments, the phantom used in conjunction with the system described above is configured to have substantially similar contrast between the target and background when utilized in MRI and CT imaging.

In some embodiments, the air pump is mechanically connected to the phantom through an air hose. In some embodiments, the air hose is connected to an air valve, which is in turn connected to a collapsible air container associated with or included within the phantom. In some embodiments, the phantom is configured to move when air is added to and/or released from the collapsible air container. In some embodiments, the phantom moves in response to air being added to or released from the collapsible air container by gliding on rails and/or wheels. In some embodiments, the air container is a bellow, but one of skill in the art would readily appreciate that the air container could be any collapsible air container. In some embodiments, multiple air containers (e.g. bellows) are used.

In some embodiments, the invention teaches a phantom designed for use with a machine capable of performing a PET scan and/or an MRI scan. In some embodiments, the phantom is designed for use with a scanner capable of performing MRI and PET scans (e.g. Biograph mMR, Siemens). In some embodiments, the phantom is configured for use with a scanner capable of simultaneous acquisition of whole-body MR and PET.

In some embodiments, the phantom includes (1) a first container that contains a first composition including a PET agent and/or an MRI agent that includes Gd, (2) a second container that contains a second composition including the PET agent and/or the MRI agent, (3) a first tube that is in fluid communication with the first container, and (4) a second tube that is in fluid communication with the second container. In some embodiments, the first container is contained within the second container. In some embodiments, the Curie value (i.e., level of radioactivity) of the first composition is higher than the Curie value of the second composition. In some embodiments, the concentration of Gd in the first composition is higher than the concentration of Gd in the second composition.

In some embodiments, a first composition including a PET agent is included in the first container, and a second composition including a PET agent is included in the second container (which houses the first container). In other words, no MRI agent is included in the first or second containers. In some embodiments, the first composition has a higher Curie value than the second composition.

In some embodiments, a first composition including an MRI agent is included in the first container, and a second composition including an MRI agent is included in the second container (which houses the first container). In other words, no PET agent is included in the first or second containers. In some embodiments, the first composition including the MRI agent has a higher concentration of Gd than the second composition including the MRI agent.

In some embodiments, the first container includes a first composition that includes a PET agent and an MRI agent, and the second container includes a second composition that includes a PET agent and an MRI agent. In these configurations, the first composition has a higher Curie value than the second composition, and the first composition has a higher Gd concentration than the second composition.

One non-limiting embodiment of the invention is depicted in FIG. 11. FIG. 11 shows first container 7001 which contains a first composition that includes a PET and/or an MRI agent. FIG. 11 also shows second container 7000 which contains a second composition that includes a PET and/or an MRI agent, and which contains the first container. Also depicted in the drawing is tube 7002, which is in fluid communication with container 7001, and tube 7003, which is in fluid communication with container 7000. Tube 7002 can be used to introduce the first composition including a PET and/or MRI agent into container 7001, and tube 7003 can be used to introduce the second composition including a PET and/or MRI agent into container 7000. In some embodiments, tubes 7002 and/or 7003 also include one or more valves that control the flow of MRI agent and/or PET agent into or out of the containers with which they are associated. In some embodiments, the first composition contained in container 7001 has a higher Curie value than the second composition contained in container 7000. In some embodiments the first composition contained in container 7001 has a higher concentration of Gd than the second composition contained in container 7000.

For each embodiment described herein in which a PET agent is included, the PET agent contained in the first composition may be of the same type as the PET agent contained in the second composition.

For each embodiment described herein in which an MRI agent is included, the MRI agent contained in the first composition may be of the same type as the MRI agent contained in the second composition.

Merely by way of non-limiting examples, the PET agents used in any of the aforementioned embodiments may comprise, consist of, or consist essentially of any of the following PET tracers: 18F (fluorine-18)-related radiotracers (e.g., 18F-fluorodeoxyglucose (18F-FDG) analogue; 18F-fluoroethyl-tyrosine (18F-FET); 18F-Fluoromisonidazole (18F-FMISO); 18F-Fluciclovine; 18F-Fluorocholine; 18F-3'-fluoro-3'-deoxythymidine (18F-FLT)); 11C (carbon-11)-related radiotracers (e.g., 11C-Acetate; 11C-Methionine; 11C-Choline); 68Ga (gallium-68)-related radiotracers (e.g., 68Ga-DOTA-pseudopeptides); 64Cu (copper-64)-related radiotracers (e.g., 64Cu-diacetyl-bis(N4-methylthiosemicarbazone) (64Cu-ATSM); combinations of the above, or substances with functional equivalency to those listed above. In some embodiments in which any radiotracer described above is used as a PET agent, the composition with a higher Curie value is from 0.01-0.2 m Curie, and the composition with a lower Curie value ranges from 0.00001 to 0.001 m Curie. In some embodiments, the compositions that include PET agents are liquid compositions that further include water. In some embodiments, the compositions that include PET agents are liquid compositions that further include saline.

In some embodiments, the MRI agent used alone or in conjunction with the PET agent, as described above, includes any of the agents including Gd described herein. In some embodiments, the composition with a higher concentration of Gd has a concentration of Gd in the range of $5 \times 10^{-3}$ Mol/mL to 0.25 Mol/mL. In some embodiments, the composition with a lower concentration of Gd has a concentration of Gd in the range of $5 \times 10^{-4}$ Mol/mL to $5 \times 10^{-3}$ Mol/mL. In some embodiments, the composition including the MRI agent is a liquid composition that further includes water. In some embodiments, the composition including the MRI agent is a liquid composition that includes saline.

In various embodiments, the system includes an MRI scanner, in addition to a phantom suitable for MRI (as described above), air pump (as described above), and computer-operated control module (as described above), and any additional components associated with the system as described herein. In certain embodiments, the MRI scanner is positioned/configured to image the phantom by any standard MRI method, or any other MRI method described herein. Merely by way of non-limiting example, as demonstrated in FIG. 8, MRI scanner 100 can be positioned/configured to scan phantom 200 when it is moved into MRI scanner 100 along bed 101.

FIG. 8 depicts a non-limiting exemplary system 1000, which includes computer 600 that includes RSD controller module 601. The computer 600 controls the function of RSD air pump 500 through RSD controller module 601. The air pump 500 is connected to input valve 300 through air hose 700. Air is delivered through air hose 700 and into air bellow 302, which in turn modulates the position of water box 205 that includes weak Gd water. Water box 205 contains target 204 that includes low-concentration Gd gel. Target 204 in turn includes target 201 that includes high-concentration Gd gel. Box 200 includes background water. The system 1000 also includes air output valve 301, plastic rail carrier 203 (which is shown with wheels), ruler 202, bed 101, and MRI scanner 100. In some embodiments, the invention teaches the system depicted in FIG. 8 without the MRI scanner and/or bed.

In various embodiments, the system includes a CT scanner, in addition to a phantom (as described above), air pump (as described above), and computer-operated control module (as described above). In certain embodiments, the CT scanner is positioned/configured to image the phantom. Merely by way of non-limiting example, as demonstrated in FIG. 9, CT scanner 800 can be positioned/configured to scan phantom 200 when it is moved into CT scanner 800 along bed 801. As demonstrated in FIG. 9, in some embodiments in which the CT scanner is incorporated in the system, a linear actuator and infrared box, such as the linear actuator 1200 and infrared control box 1100, are also included in the system.

FIG. 9 depicts a non-limiting exemplary system 2000, which includes computer 4000 that includes RSD controller module 4001. The computer 4000 controls the function of RSD air pump 500 through RSD controller module 4001. The air pump 500 is connected to input valve 300 through air hose 700. Air is delivered through air hose 700 and into air bellow 302, which in turn modulates the position of water box 205 that includes weak Gd water. Water box 205 contains target 204 that includes low-concentration Gd gel. Target 204 in turn includes target 201 that includes high-concentration Gd gel. Box 200 includes background water. The system 2000 also includes air output valve 301, plastic rail carrier 203 (which is shown with wheels), ruler 202, bed 801, and CT scanner 800. The system 2000 further includes linear actuator 1200 and infrared box 1100. In system 2000, the computer 4000 and RSD controller module 4001 control the motion of linear actuator 1200 through an electrical signal provided through electrical cable 3000. In some embodiments, the invention teaches the system depicted in FIG. 9 without the MRI scanner and/or bed. In some embodiments, the invention teaches the system depicted in FIG. 9 without the linear actuator or infrared box.

In various embodiments, the invention teaches a system that includes a machine capable of performing a PET scan. In some embodiments, the machine is a combination PET/MRI scanner, as described above. In some embodiments, system further includes a phantom suitable for a PET and/or MRI scan (as described above), air pump (as described above), and computer-operated control module (as described above), and any additional components associated with the systems as described herein. In certain embodiments, the PET and/or PET/MRI and/or MRI scanner is positioned/configured to image the phantom by any standard PET, MRI/PET, or MRI method. Merely by way of non-limiting example, as demonstrated in FIG. 10, MRI/PET scanner 5000 can be positioned/configured to scan phantom 200 when it is moved into MRI/PET scanner along bed 5001.

Figure 10:
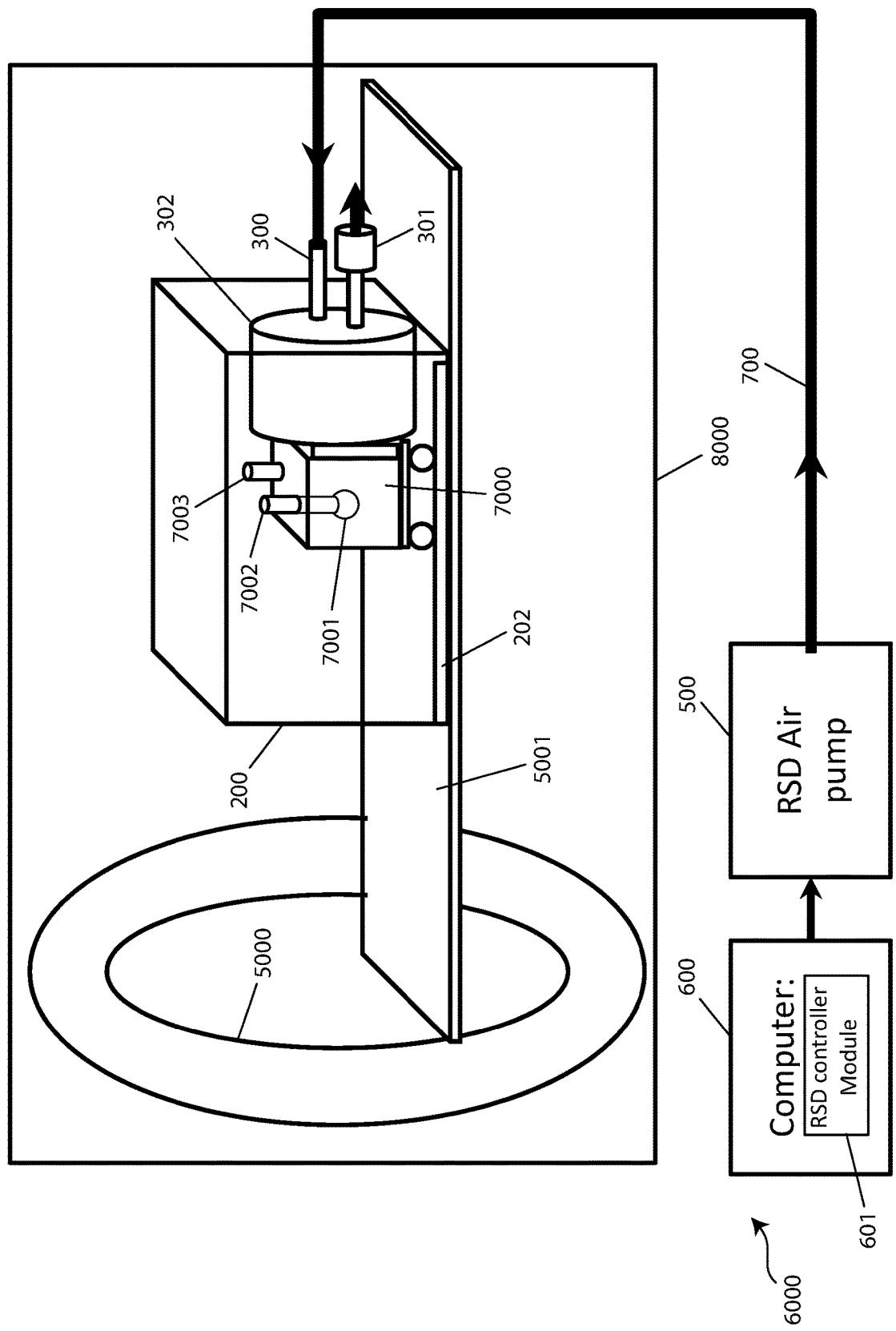
FIG. 10 depicts, in accordance with an embodiment of the invention, a phantom setup that can be used for MRI and PET imaging. As shown, many of the components are the same as those of the system depicted in FIG. 8. However, water box 200 houses a container 7000 which includes a first composition that contains a PET and/or an MRI agent. Included within container 7000 is an additional container 7001 that contains a second composition that includes the PET and/or the MRI agent. The system also includes a tube 7002 that is in fluid communication with the container 7001, and a tube 7003 that is in fluid communication with container 7000.

FIG. 10 depicts a non-limiting exemplary system 6000, which includes computer 600 that includes RSD controller module 601. The computer 600 controls the function of RSD air pump 500 through RSD controller module 601. The air pump 500 is connected to input valve 300 through air hose 700. Air is delivered through air hose 700 and into air bellow 302, which in turn modulates the position of container 7000. Container 7000 houses container 7001 which contains a first composition that includes a PET agent. Container 7000 also contains a second composition that includes a PET agent. The first composition contained within container 7001 has a higher Curie value than the second composition contained within container 7000. Tube 7002 is in fluid communication with container 7001, and tube 7003 is in fluid communication with container 7000. All of the other components of the system are as described in the system shown in FIG. 8. In addition to or instead of the PET agent, the first and second compositions may include an MRI agent, as described above. In some embodiments, water box 200 is not included. In some embodiments, the compositions are liquid compositions that contain either water or saline in addition to the PET agent and/or MRI agent.

In various embodiments, the invention teaches a method that includes operating a system that mimics the respiration of a subject. In some embodiments, the system includes: (1) a phantom that includes: a target including a high-concentration gadolinium (Gd) gel, with a concentration ranging from $5\times10^{-3}$ Mol/mL to 0.25 Mol/mL; a target container containing a low-concentration Gd gel, with a concentration ranging from $5\times10^{-4}$ Mol/mL to $5\times10^{-3}$ Mol/mL; and a water container containing weak-concentration Gd water ranging from $5\times10^{-6}$ Mol/mL to $5\times10^{-5}$ Mol/mL; wherein the target is embedded in the target container and stabilized with the low-concentration Gd gel, and the target container is sealed in the water container; (2) an air pump mechanically connected to the phantom (e.g. by any manner described herein); and (3) a computer-operated controller module; wherein the computer-operated controller module is configured to modulate an air pressure generated by the air pump which in turn modulates the position of the phantom. In some embodiments, the operated system further includes a linear actuator. In some embodiments, the operated system further includes an external surrogate operably connected to the linear actuator. In some embodiments, in addition to modulating air pressure, the computer-operated controller module of the operated system is also configured to modulate the position of the external surrogate via the linear actuator. In some embodiments, the method includes operating the system by controlling the rate of simulated respiration, as described herein. In some embodiments, the method further includes performing an MRI scan while the system is simulating respiratory motion. In some embodiments, the method further includes performing a CT scan while the system is simulating respiratory motion.

In various embodiments, the invention teaches a method that includes operating an MRI scanner and scanning a phantom that is included within a system described herein. Merely by way of example, in some embodiments the invention teaches operating an MRI machine to scan the phantom shown in FIG. 8.

In various embodiments, the invention teaches a method that includes operating a CT scanner and scanning a phantom that is included within a system described herein.

Merely by way of example, in some embodiments the invention teaches operating a CT scanner to scan the phantom shown in FIG. 9.

In some embodiments, the invention teaches a method that includes operating an MRI scanner or an MRI/PET scanner and scanning a phantom that is included within a system described herein. Merely by way of example, in some embodiments the invention teaches operating an MRI or MRI/PET scanner to scan the phantom shown in FIG. 10.

In some embodiments, the invention teaches a kit. In some embodiments, the kit includes one or more of (1) a phantom that includes: a target including a high-concentration gadolinium (Gd) gel, with a concentration ranging from $5 \times 10^{-3}$ Mol/mL to 0.25 Mol/mL; a target container containing a low-concentration Gd gel, with a concentration ranging from $5 \times 10^{-4}$ Mol/mL to $5 \times 10^{-3}$ Mol/mL; and a water container containing weak-concentration Gd water ranging from $5 \times 10^{-6}$ Mol/mL to $5 \times 10^{-5}$ Mol/mL; wherein the target is embedded in the target container and stabilized with the low-concentration Gd gel, and the target container is sealed in the water container; (2) an air pump configured to be mechanically connected to the phantom; and (3) a computer-operated controller module; wherein the computer-operated controller module is configured to modulate an air pressure generated by the air pump which in turn modulates the position of the phantom. In some embodiments, the kit further includes one or more of any of the additional components of the systems described herein. In some embodiments, the additional components include one or more of the following: a linear actuator, an external surrogate, an air hose, an input valve, an outlet valve, a rolling carrier, a measuring ruler, a computer, an electrical cable, and a marker.

In some embodiments, the invention teaches a kit that includes any phantom suitable for PET and/or MRI scanning described herein. In some embodiments, the kit further includes one or more compositions that include one or more PET agents described herein. In some embodiments, the kit further includes instructions for performing a PET and/or MRI scan using one or more suitable phantoms, as described herein. In some embodiments, the kit includes one or more components of the systems described herein that are useful for MRI and/or PET scanning.

EXAMPLES

The following examples are not intended to limit the scope of the claims to the invention, but are rather intended to be exemplary of certain embodiments. Any variations in the exemplified methods which occur to the skilled artisan are intended to fall within the scope of the present invention.

Introduction

Four-dimensional (4D) computed tomography (CT) is currently a standard in radiotherapy planning to assess respiratory motion and determine treatment margins for target tumors. An internal target volume (ITV), derived from the union volumes of all breathing phases or a maximum intensity projection, is typically used to derive the planning target volume (PTV) for the majority of treatment planning and delivery techniques in which motion is an issue. Use of an ITV generally provides an adequate margin on the target, however, it may also lead to increased potential toxicity to surrounding healthy tissue. Phase-resolved target definition and motion management are highly desired in clinical practice. However, implementation of phase-resolved imaging has several technical difficulties due to the limitations of current acquisition hardware and respiratory phase reconstruction software, especially for reconstruction based on retrospective sorting of sequential axial acquisitions of 3D-CTs using an external respiratory surrogate. This imaging process is prone to manifest motion artifacts caused by irregular breathing patterns, and low spatiotemporal resolution. It has been reported that 90% of scans have at least one artifact in a retrospective study on 50 patients with lung and abdominal tumors. Recent developments in 4D-MRI techniques provide alternative solution(s) to the motion assessment problems in radiotherapy. Various early efforts have been made toward developing real-time 3D volumetric acquisition, however, the trade-off between spatial and temporal resolution has limited its application in tumor targeting and motion assessment. An alternative strategy has been recently proposed which will improve the frame rate and in-plane spatial resolution based on respective sorting of 2D multi-slice acquisitions. However, the slice resolution must remain relatively low (i.e. 3-10 mm) in order to maintain satisfactory 2D slice profile and signal or to reduce the total scan time. More importantly, the image reconstruction, similar to 4D-CT, still relies on sorting of post-reconstructed slice images, so it is vulnerable to irregular breathing and anisotropic spatial resolution, and may suffer target stretching and partial missing artifacts. Therefore, currently available 4D techniques have limited ability to provide an optimal solution for phase-resolved target imaging in radiotherapy. We have recently reported a novel 4D MRI method based on self-gating motion surrogate and retrospective k-space sorting. The 4D acquisition is completed in a fixed scan time and provides both high spatial and high temporal resolution. This approach resolves the respiratory phase sorting and reconstruction all in k-space. One of the important advantages of the technique is that the phase sorting is self-gated without pre-scan selection or in-scan external respiratory surrogate acquisition. This technique allows the removal of motion outliers and artifacts without interrupting the acquisition. Another major advantage of the technique is that it provides isotropic high spatial resolution, which enables accurate evaluation of phase-based target definition and motion measurement.

The goals of the studies reported below were to conduct a geometric validation of the 4D MRI technique using a MRI/CT compatible respiratory motion phantom, and to compare the 4D MRI technique to 4D CT using the motion phantom. Clinical imaging results and a description of the imaging sequence development have been previously reported.

Methods

4D MRI Acquisition

The 4D-MRI sequence is based on spoiled gradient echo-based 3D projection reconstruction (PR) sequence with self-gating (SG) at 3T. FIG. 1 illustrates the flowchart of 4D image acquisition. Radial projections in k-space are continuously collected in a 2D golden means ordering that allows for flexible retrospective data sorting. The respiration-induced shift of the imaging target is recorded by a group of 2 superior-inferior (SI) k-space projections (i.e. SG lines), which are inserted every 15 radial projections (i.e. imaging lines). The temporal interval between 2 SG lines is approximately 98 ms (FIG. 1(A)). A total of 86160 radial projections and 5744 SG lines are obtained in 8 min in the scans used in the current study. The 8 minute acquisition time was determined to provide an adequate number of k-space projections based on our earlier work in human abdominal imaging studies. Respiratory phase is resolved by extracting the respiratory signal from SG lines. The Fourier transform of an SG line represents a 1D projection of the entire imaging volume. The respiratory motion signal was extracted by applying principal component analysis (PCA) to the projection profile time series from all channels. As shown in FIG. 1(B), the respiratory motion of the target is plotted as the relative SI displacement derived from SG lines. On this curve, the respiratory cycles are identified by the time period of two neighbor expiratory peaks. Motion is sampled by SG every 98 ms (i.e. 17×TR, due to the acquisition of 15 imaging lines and 2 SG lines), which is much shorter than the typical respiratory cycle lengths (>4 sec, typically). To sort the phase data, respiratory cycles are temporally-evenly divided into 10 bins. The k-space data with the same phase number for all respiratory cycles are assigned to a final nominal phase bin. As shown in FIG. 1(C), the phase information of each bin (e.g. bin-6) is contributed by that same bin (e.g., all bin-6 s) for all validated cycles (FIG. 1(B)). To suppress motion artifacts, segments with the abnormal time period or inconsistent positions (≥mean±two standard deviations) are considered to be outliers (e.g. dash-circles in FIG. 1(C)), and are excluded from phase binning. After sorting k-space data, the image of each individual phase 126 is reconstructed using a self-calibrating sensitivity encoding (SENSE) reconstruction method, which uses the receiver coil sensitivity information to suppress aliasing artifacts. No other correction, such as bias field, was used in the 4D reconstruction. In the phantom experiments, the cubic imaging volume of 4D-MRI was centered on the moving phantom with the following imaging parameters: FOV (300×300×300 mm3), spatial resolution (1.56×1.56×1.56 mm3), flip angle (10 degree), TR/TE=5.8/2.6 ms, readout bandwidth=399 Hz/pixel, non-selective water excitation RF pulse. The reconstructed 4D-MRI image set consists of 10 temporal phases.

MRI-CT Respiratory Motion Phantom

Figure 2:
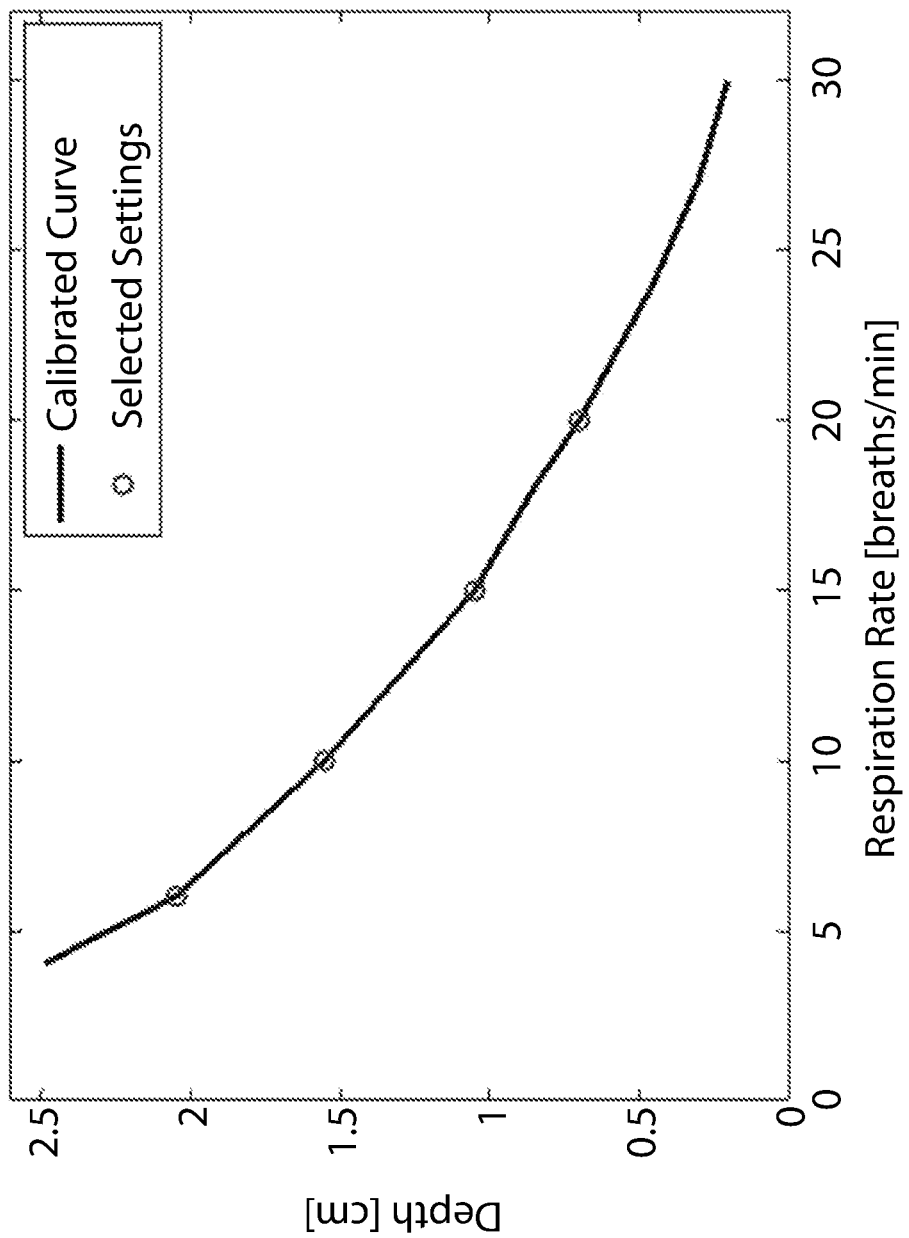
FIG. 2 depicts, in accordance with an embodiment of the invention, motion calibration curve of the dynamic phantom as a function of respiration rate (RR). The red circles indicate that four RR settings (6, 10, 15, and 20) are used in this study.
Figure 4A:
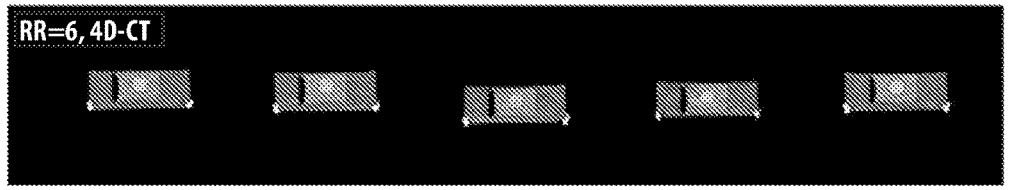
FIG. 4 depicts, in accordance with an embodiment of the invention, phase-resolved 4D phantom images are demonstrated by phase 1, 3, 5, 7 and 9. The images 4D-CT images (A, C, E, and G) are compared with 4D-MRI images (B, D, F, and H) at four different respiratory rates (RR=6, 10, 15 and 20).
Figure 4B:
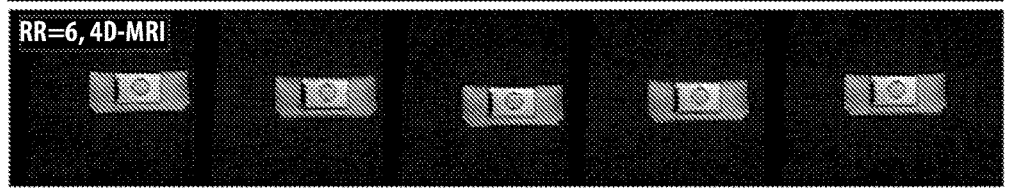
Figure 4C:
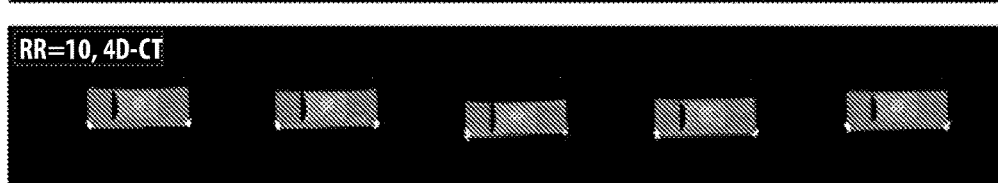
Figure 4D:
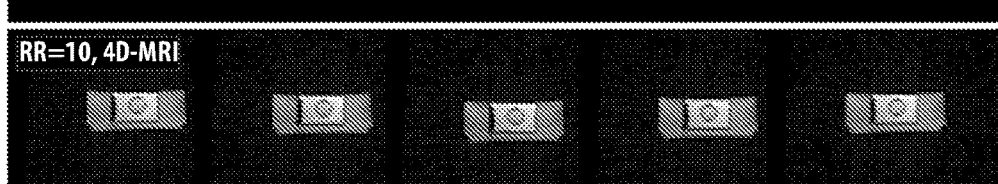
Figure 4E:
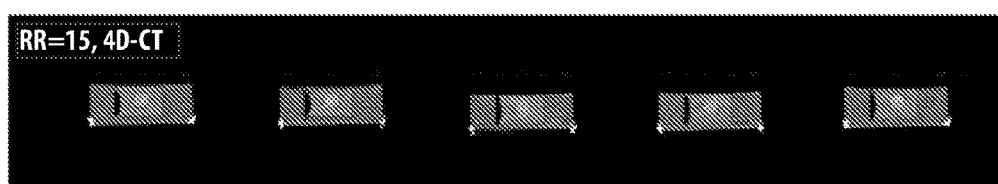
Figure 4F:
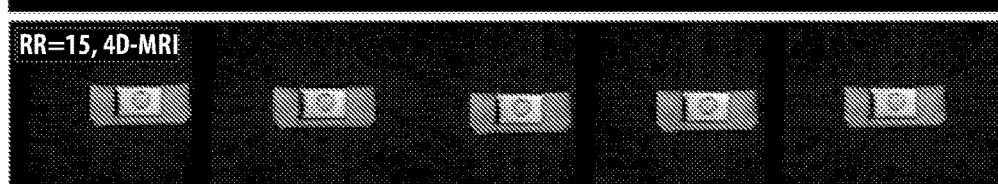
Figure 4G:
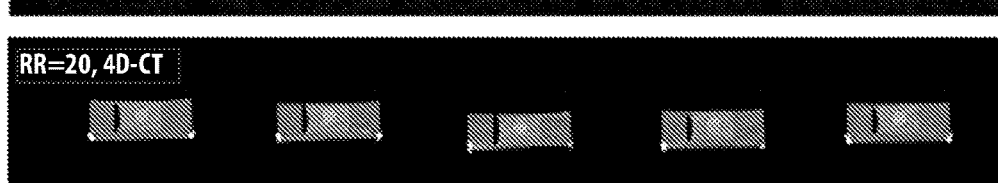
Figure 4H:
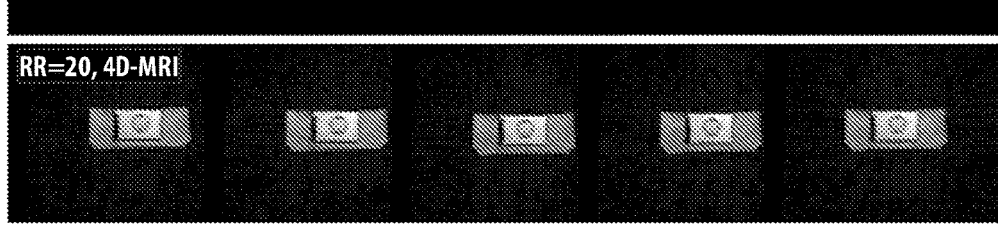
Figure 5A:
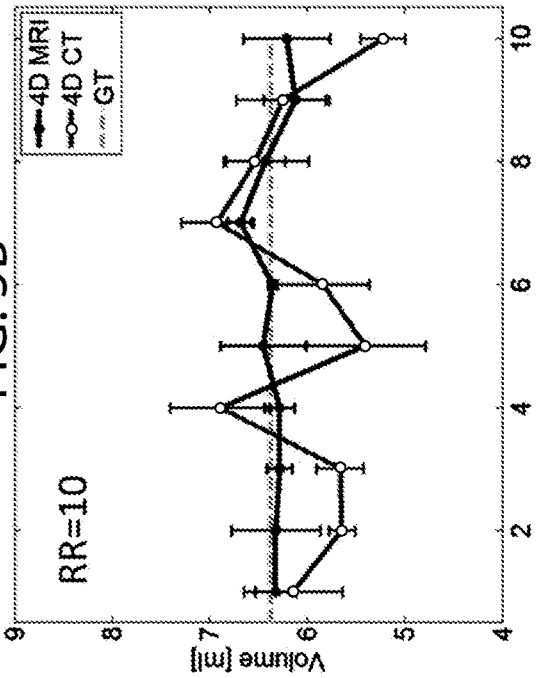
FIG. 5 depicts, in accordance with an embodiment of the invention, phase-resolved target volume is compared between 4D-MRI and 4D-CT at different respiratory rates (RR). (A) RR=6, (B) RR=10, (C) RR=15, and (D) RR=20. The ground truth (green dash line) is 6.37 ml.
Figure 5B:
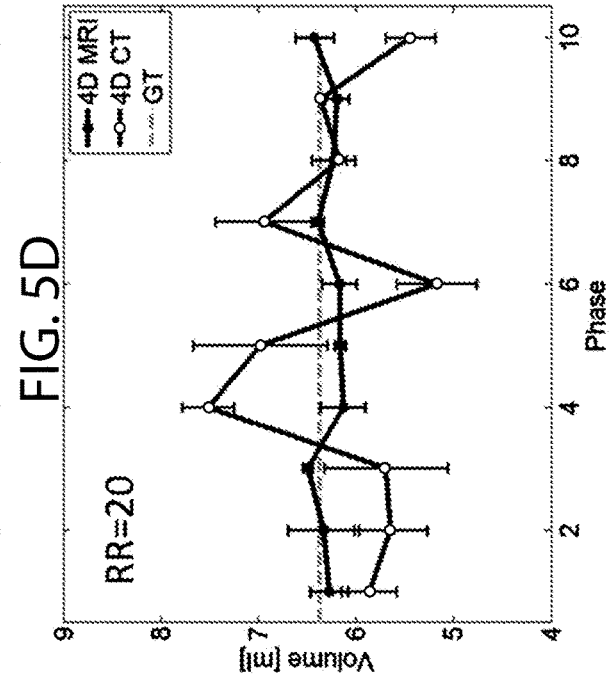
Figure 5C:
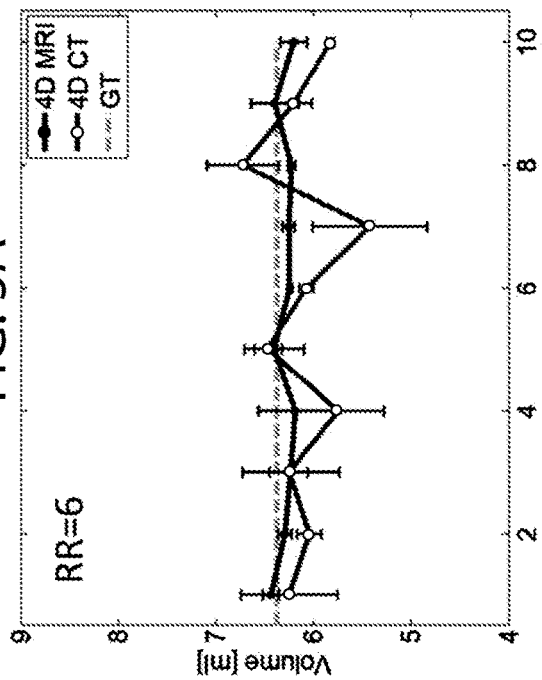
Figure 5D:
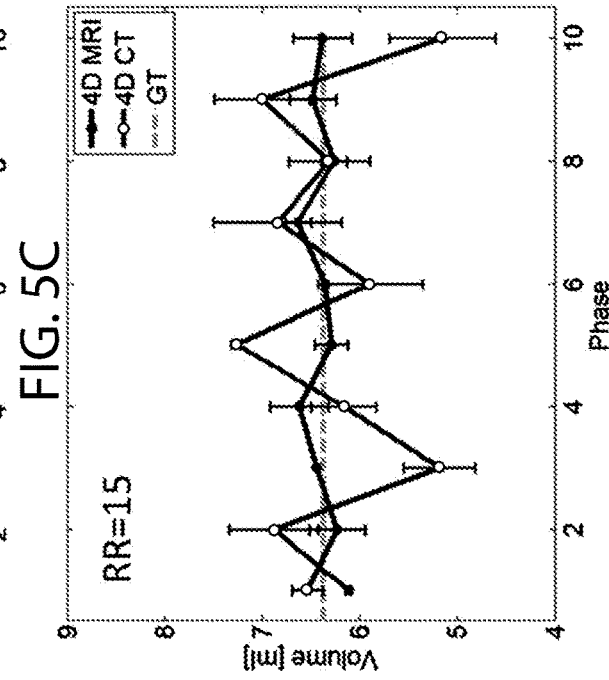

An MRI-CT compatible phantom was designed to validate the performance of the 4D MRI sequence and 4D CT imaging. A spherical target (diameter 23 mm, volume 6.37 ml) filled with high-concentration gadolinium (Gd) gel was embedded into a plastic box (35×40×63 mm3) and stabilized with low-concentration Gd gel. The plastic box was further stabilized with plastic supports and sealed into a water container. The phantom was designed to have similar contrast between target and background for both MRI and CT imaging. The phantom can produce superior-inferior motion driven by an air pump which is placed outside the MRI room. Human respiratory motion was mimicked using the controller module of the Dynamic Breathing Phantom (Model RS-1500, Radiology Support Devices (RSD), TM), which has the capability to produce various human respiratory rates (2-20 s/cycle) and breathing depths (3-30 mm). The RSD controller model is able to provide two respiratory signals: pressured air generated by the air pump and mechanical motion generated by the linear actuator. The former is used to drive the phantom in the SI direction during both CT and MRI scans, and the latter output is used to drive the motion surrogate in the anterior-posterior (AP) direction for 4D-CT scans. In our experiments, the motion system simulated the human breathing patterns using diaphragm motion (target) and chest wall motion (RPM box). To achieve this, the external surrogate (RPM box) was driven by the same respiratory rate and amplitude of target input signal but with 90 degree phase shift. Before experiments, the system was calibrated to synchronize the two motions and this synchronization was further verified with video recordings. Therefore, motion artifacts due to uncoordinated external surrogate motion were eliminated. The respiratory rates and depth were calibrated by tuning the controller parameter and adjusting input and output air volume. The calibrated curve as a function of respiratory rate and depth is shown FIG. 2. As a result, the phantom is able to produce human-type breathing patterns between 4 to 30 respiratory cycles per minute. In addition, the respiration rate (RR) is inversely proportion to breathing depth: it can produce a fast respiration rate with shallow breathing depth (e.g. 30/min, 2 mm), and a slow respiration rate with deep breathing (e.g. 6/min, 20 mm). Four respiratory rate settings, 6, 10, 15 and 20 per min, were selected to be used in MRI and CT acquisitions with their corresponding respiratory cycle times and depths of 10 s/20 mm, 6 s/15 mm, 4 s/10 mm, and 3 s/7 mm. During scans, the ground truth for the motion was obtained from input signals and validated by real-time video recordings.

4D CT Acquisition

4D CT images were acquired using a GE CT590 CT scanner with cine mode. Before each 4D CT, the phantom was scanned in helical mode to acquire a static 3D image. During the 4D-CT scans, a linear actuator operated by the RSD motion controller was used to produce external respiratory AP motion. An RPM plastic box labeled with infrared markers was placed on the tip of the linear actuator, where it can be tracked by the Varian RPM system during 4D-CT scans. The AP motion of the linear actuator was set to be 90° degrees (orthogonal) to the SI motion of output of air pump.

Images were acquired for a cine duration that was set to 1.5 s longer than the estimated respiratory period from the RPM system. Scan parameters were set as follows: 1 s gantry rotation, 0.2 s cine interval. The slice thickness was set to 2.5 mm for motion ranges larger than 2.0 cm, and 1.25 mm for those 2.0 cm or less. The 4D-CT images were reconstructed by GE Advantage 4D software. Specifically, raw 4D-CT cine images were sorted retrospectively into respiratory phase-based bins. Each CT slice in the raw cine images was assigned a phase number according to the temporal correlation between the RPM trace and CT data acquisition. Then the images with the same phase were used to construct 3D-CT data sets, and sorted retrospectively into 10 respiratory phase (i.e., from 0% to 90% phase at 10% intervals).

Motion and Geometric Qualification

The 4D-CT and MRI images were imported into a treatment planning system (Varian Eclipse v11.0) and image segmentation software (ITK-SNAP (See P. Yushkevich, et al. "User-guided 3D active contour segmentation of anatomical structures: Significantly improved efficiency and reliability," Neuroimage, 31, 1116-28 (2006)) for geometric qualification. 4D structure sets were created for the 4D-CT and 4D-MRI scan sets using the 4D-CT module in Eclipse. The target motion visualized with the CT and MRI 4D image sets was tracked through the positions of centroids of spheres in each individual phase in each dataset. Meanwhile, the ground truth positions of the sphere were measured in the recorded video and real-time 2D MRI sequence images. Contours of the sphere targets were manually drawn for all the phase-resolved images by two users. Based on the drawn contours, the volumes were measured using the software. The ground truth volume of the sphere (VGT) was calculated from the physical parameters (diameter 2.3 cm, volume 6.37 ml), and validated by the static helical 3D-CT image. For the 4D images, the volume deviations were calculated by comparing the volume difference between measurements and the ground truth volume, dV=VMeasured−VGT, and the percentage of difference dV %=(VMeasured−VGT)/VGT, as well as its absolute percentage difference |dV %|. Here, we assumed that volume deviation represents motion-introduced errors in the gross tumor volume (GTV) on actual patient 4D CT or MRI scans.

To examine the geometrical accuracy of the target representation, the imaged targets were further characterized as a spheroid with semi-major axis length, a, and semi-minor axis length, b. To obtain the axis lengths, the DICOM structure sets containing the contours of each individual phase were exported and post-processed in MATLAB (TM, v8.1). Two geometric parameters of the spherical targets, flattening and eccentricity, were calculated. The flattening (F) measures the ratio of the difference of the two axis lengths to the semi-major axis length F=(a−b)/a, and eccentricity (E) describes the deviation from being circular, E=$\sqrt{a^2+b^2}$/a. Finally, the Mann-Whitney test (U-test) was used to compare the performance of 4D MRI and CT in both motion tracking and phase-based target definition.

Results

Results of Phase-Resolved Reconstruction

4D MRI and 4D CT scans were acquired for the dynamic phantom operated 228 with 4 respiration rates (RRs): 6, 10, 15, and 20 per min. Each 4D scan was reconstructed into 10 phases. FIG. 3 illustrates phase-resolved images from the 4D-CT and 4D-MRI datasets of the phantom, compared with its static 3D-CT image. As shown in the figure, the sphere targets in the CT images have similar grey level and contrast as the ones in the MRI images. FIG. 4 visually demonstrates the differences between the 4D-CT and MRI images, using images from individual phases 1, 3, 5, 7 and 9 and acquired at different respiratory rates. As shown 4D-CT images in FIGS. 4(A, C, E, and G), the images of phase 1 are visually similar to the static image, whereas other phase images appear to have more or less motion artifact, e.g., target stretching (phase 5, RR=15), and squeezing or partially missing information (phase 3, RR=15). It is also apparent that images acquired during slow motion mode (RR=6) appear to have fewer artifacts. In contrast to the 4D-CT, the phase-resolved 4D-MRI images do not have similar motion artifacts to those seen in the 4D-CT images. As shown in 4D-MRI in FIGS. 4 (B, D, F and H), all images at different phases and different respiratory rates have nearly equivalent image quality (e.g. compare the phase 3 at RR=20 4D-MRI vs the phase 3 4D-MR image at RR=6). The results indicate that 4D-MRI has robust spatial-temporal resolution at various respiratory rates.

Results of Phase-Resolved Geometry Measures

Figure 6A:
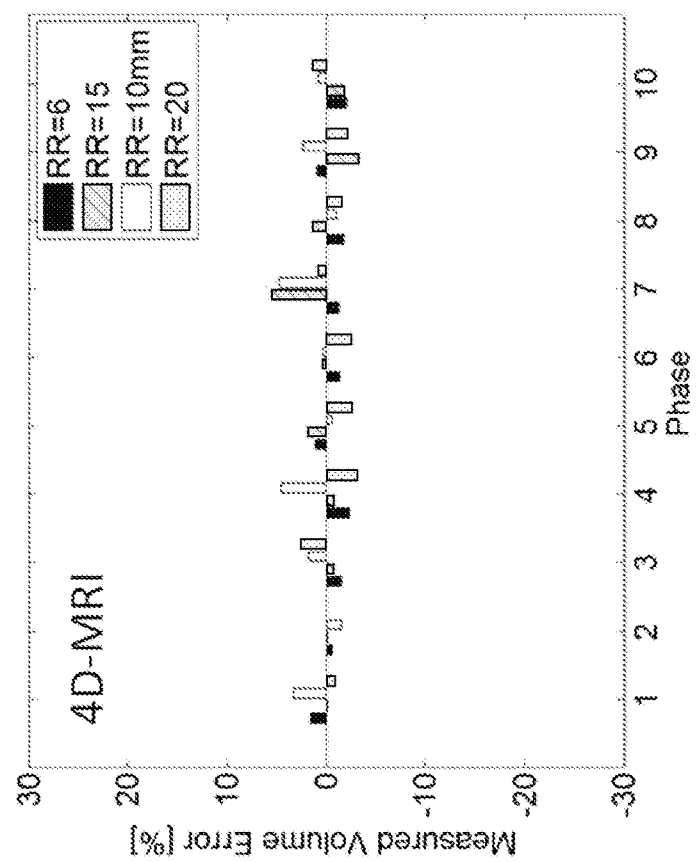
FIG. 6 demonstrates, in accordance with an embodiment of the invention, phase-resolved target volume measurement errors dV at different respiratory rates (RR=6, 10, 15 and 20). (A) 4D-CT, and (B) 4D-MRI.
Figure 6B:
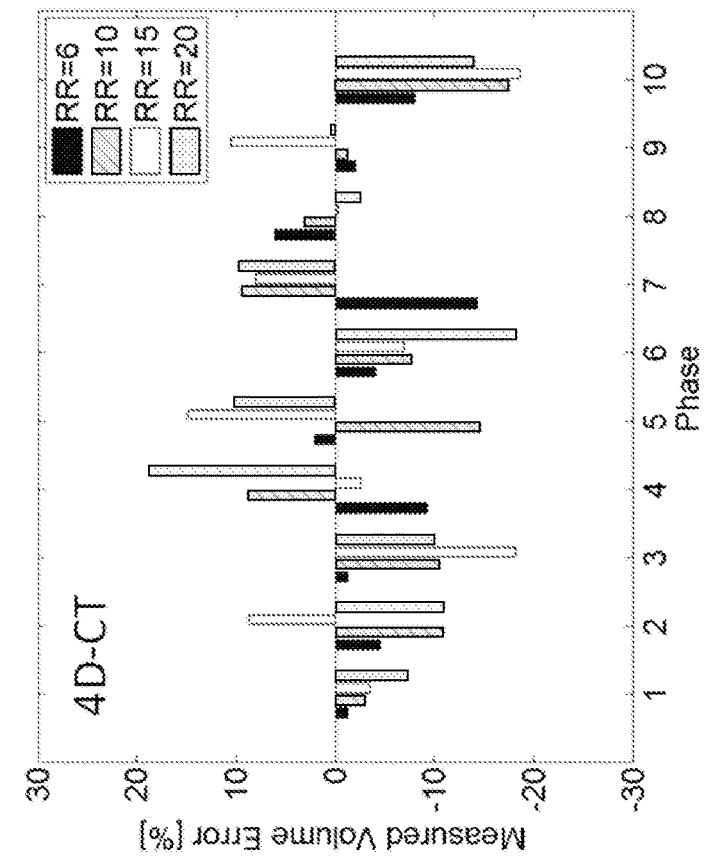
Figure 7A:
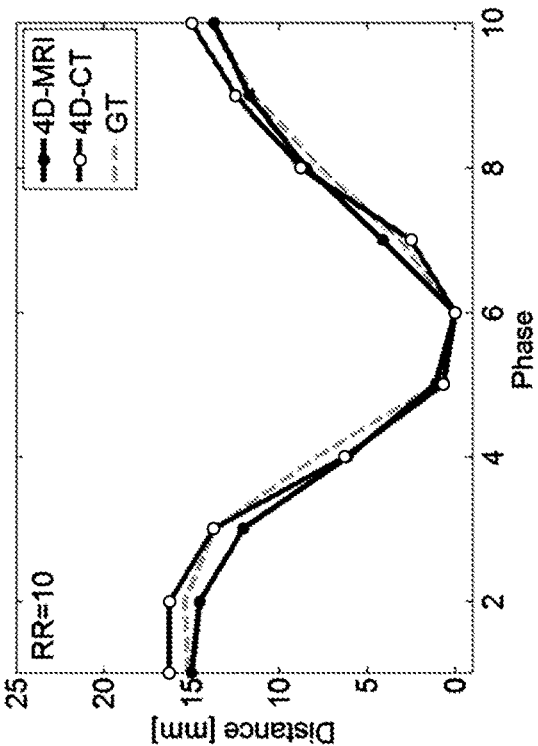
FIG. 7 demonstrates, in accordance with an embodiment of the invention, phase-resolved target motion is compared between 4D-MRI and 4D-CT at different respiratory rates (RR). (A) RR=6, (B) RR=10, (C) RR=15, and (D) RR=20. The ground truth (GT, green dashed line) is measured from video recording.
Figure 7B:
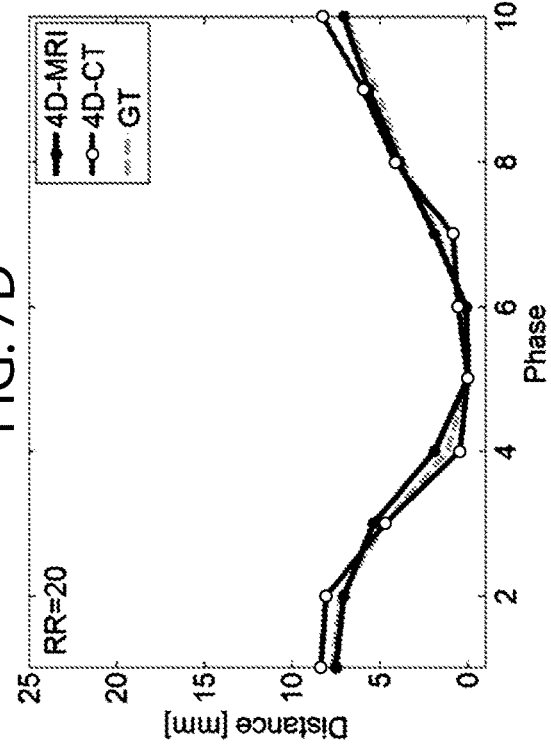
Figure 7C:
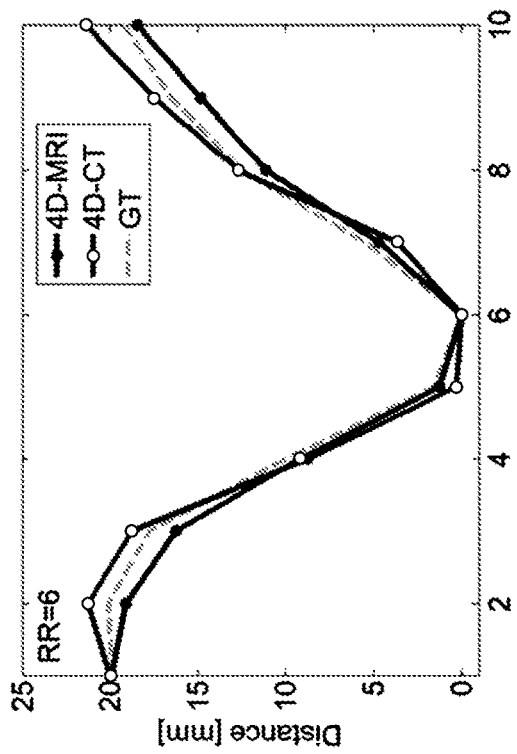
Figure 7D:
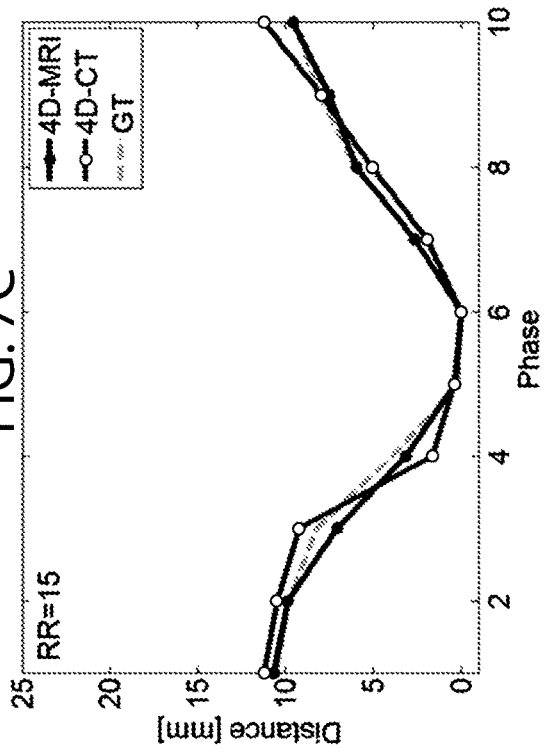

The target volumes were contoured and measured in both planning and segmentation software by two users. The results of Wilcoxon tests indicated that there was no significant difference between contours drawn by different operators (p=0.0003 for CT images, p<<0.0001 for MRI images). FIG. 5 shows the measured volumes plotted as a function of phase. For the same RR setting, target volumes in 4D-MRI are very close to the ground truth volume, whereas some phases of 4D-CT demonstrate a large volume measurement error. As shown in CT images of FIG. 4(F) for RR=15, the target sphere is truncated at phase 3 (5.18 ml), whereas it is stretched at phase 5 (7.27 ml). This is due to motion artifact and phase-sorting error in the 4D-CT reconstruction. Given the ground truth volume (6.37 ml), the percentage deviations of volume (dV %) for 4 settings were calculated, shown in FIG. 6.

Table I summarizes the performance of the 4D-CT and 4D-MRI in phase-resolved volume measurement. For 4D-CT, the absolute volume error increases with increasing respiratory rate, from 5.3±4.3% (RR=6) to 10.3±5.9% (RR=20). The minimum and maximum phase-resolved volumes also show the same trend. For 4D-MRI, volumetric errors at different RRs are all smaller than 3%, and are independent of the respiratory rates. Combining all RR settings, the overall volumetric errors are 8.4±5.6% for 4D-CT, and 1.8±1.3% for 4D-MRI. The Mann-Whitney test was used to examine the statistical difference of the 4D-CT and 4D-MRI in term of volume measurement, with a result of p=0.027.

TABLE I

Target volumes measured by phase-resolved 4D-MRI and 4D-CT images. The accuracy is evaluated by the percentage deviation to the ground truth (6.37 ml), and is illustrated by minimum and maximum volumes.

| Phantom Respiratory Rate | Ground Truth Volume | 4D-CT Target Volume (ml) | | 4D-CT Volume Error | 4D-MRI Target Volume (ml) | | 4D-MRI Volume Error |
|---|---|---|---|---|---|---|---|
| per min | (ml) | Min | Max | \|dV\| (%) | Min | Max | \|dV\| (%) |
| 6 | 6.37 | 5.42 | 6.72 | 5.3 ± 4.3 | 6.18 | 6.43 | 1.5 ± 0.5 |
| 10 | 6.37 | 5.22 | 6.93 | 8.7 ± 5.2 | 6.12 | 6.68 | 1.6 ± 1.7 |
| 15 | 6.37 | 5.15 | 7.27 | 9.2 ± 6.4 | 6.23 | 6.63 | 2.1 ± 1.6 |
| 20 | 6.37 | 5.17 | 7.52 | 10.3 ± 5.9 | 6.13 | 6.49 | 1.8 ± 1.0 |

The results of the flattening and eccentricity metrics in 4D-CT and 4D-MRI are compared in Table II. Similar to the trend of the volume measurements, the mean values of flattening and eccentricity for 4D-CT also increase with increasing respiratory rate. The results indicate that fast target speed introduces more motion artifacts, causing large deviation from the original sphere shape. For 4D-MRI, however, the geometric deviations are both much smaller than the results from 4D-CT, and remain stable when the respiratory rate increases. The results of Mann Whitney tests on the two parameters, p=0.001 for flattening, and p=0.0005 for eccentricity, suggest that the performance of 4D-CT and 4D-MRI is significantly different. Together with the volume measurements, the overall results suggest the proposed 4D MRI is significantly superior to CT in term of phase-based target definition and geometric measures.

TABLE II

Geometric parameters measured by phase-resolved 4D-MRI and 4D-CT images.

| Phantom Respiratory Rate per min | Flattening (F) | | | | Eccentricity (E) | | | |
|---|---|---|---|---|---|---|---|---|
| | 4D-CT | | 4D-MRI | | 4D-CT | | 4D-MRI | |
| | Max | Mean | Max | Mean | Max | Mean | Max | Mean |
| 6 | 0.24 | 0.08 ± 0.06 | 0.09 | 0.03 ± 0.04 | 0.65 | 0.32 ± 0.22 | 0.32 | 0.19 ± 0.15 |
| 10 | 0.25 | 0.12 ± 0.07 | 0.10 | 0.05 ± 0.04 | 0.66 | 0.44 ± 0.15 | 0.33 | 0.21 ± 0.18 |
| 15 | 0.23 | 0.13 ± 0.08 | 0.07 | 0.05 ± 0.02 | 0.64 | 0.46 ± 0.16 | 0.36 | 0.25 ± 0.11 |
| 20 | 0.24 | 0.16 ± 0.07 | 0.07 | 0.03 ± 0.02 | 0.68 | 0.47 ± 0.13 | 0.36 | 0.22 ± 0.12 |

Results of Phase-Resolved Motion Detection

The target motion was measured by tracking the centroid of sphere of each individual phase. The ground truth for the motion was obtained from input signal and video recording. To evaluate the comparison of the methods, motion phase and amplitude of targets were measured. FIG. 7 shows the phase-resolved target positions measured by 4D-CT and 4D-MRI versus the ground truth. With increase of RRs, the inhale phase (the valley on the curve) shifts to the center (from phase 6 to phase 5) of the curve. Overall motion phase detected by each of the two modalities matches the ground truth well.

Motion amplitudes at different respiratory rates have been calculated, and are listed in Table III. The motion amplitude decreases with increase of respiratory rate, ranging from 7.7 to 20.1 mm. The results suggest that the two modalities achieve similar accuracy in term of detection of motion amplitudes, although the values from the 4D-MRI are numerically better. Note that the spatial resolution of the 4D-CT [1.27×1.27×1.25 mm] at RR=10, 15 and 20 is comparable to the resolution of the 4D-MRI [1.56×1.56× 1.56 mm], except the slice thickness for the RR=6 4D-CT scans has to be increased to 2.5 mm due to the scan coverage requirements. The Mann-Whitney test shows that the motion detection using the 4D MRI was statistically equivalent to that with 4D CT (p=0.828). In summary, the results indicate 4D MRI can be used to accurately define target geometry and volume in each phase, and equivalent (or better) performance with 4D CT for measuring target motion range.

TABLE III

The motion amplitude measured by 4D-CT and 4D-MRI at different respiratory rates. Here, motion amplitude is the difference between minimum and maximum moving distance, and the ground truth is obtained by measurement of the motion marker in the acquired video.

| Phantom Respiratory rate per min | Ground-Truth Motion Amplitude (mm) | 4D-CT Motion Amplitude (mm) | 4D-CT Motion Amplitude Error (mm) | 4D-MRI Motion Amplitude (mm) | 4D-MRI Motion Amplitude Error (mm) |
|---|---|---|---|---|---|
| 6 | 20.10 | 21.35 | 1.25 | 19.93 | −0.17 |
| 10 | 15.42 | 16.25 | 0.83 | 15.00 | −0.42 |
| 15 | 10.50 | 11.21 | 0.71 | 10.62 | 0.12 |
| 20 | 7.70 | 8.36 | 0.66 | 7.50 | 0.20 |

Discussion

MRI imaging has been used extensively for treatment planning of radiation therapy due to its advantage of improved soft-tissue contrast. Since no ionization is involved, MRI can provide a comprehensive therapy imaging solution for diagnosis, planning, in-treatment-room monitoring and therapy response evaluation without radiation dose to the patient. With the recent development of MRI-Linacs and other MRI-based therapy systems, MRI-based methods for in-treatment room monitoring are going to be very important for these systems. Concurrently, intensive efforts are also being devoted to using MRI as the primary simulation and planning imaging modality for radiotherapy in a number of clinical sites. In any scenario utilizing MRI for simulation, planning and/or treatment guidance, accurate 4D-MRI would be an essential component of motion management in the clinical use of MRI-guided or monitored radiotherapy Several techniques for 4D-MR have recently been proposed. However, most of these approaches still rely on either external gated or overhead pre-scans as the motion surrogate, limiting the spatiotemporal resolution and robustness of these methods to motion artifacts. The self-gating-based k-space sorted 4D-MR approach described here fundamentally solves these issues in sequence design and reconstruction algorithm. The method features a simplified scanning procedure, inherent motion artifact resistance, high isotropic spatial resolution and high temporal resolution. This study shows that the proposed 4D-MR method is superior to 4D-CT in terms of defining the target geometry and volume at each individual phase, and provides accurate measurement on motion phase and amplitude while also achieving a high and isotropic resolution in the imaging data.

To our knowledge, this work is the first comprehensive study on quality assurance of 4D-MRI in terms of phase-resolved target geometry and motion using a phantom mimicking human respiratory motion. An important part of this study was the design of a MRI/CT compatible phantom. The goal of the design was to create a phantom which was equally relevant to either imaging modality. A water-gel mixture was used because it provides a typical background soft tissue signal for both CT and MR. To produce contrast in the target, high concentration Gd was diluted in the target sphere, in order to create better SNR for both CT and MR. The plastic outside of the target also ensured a clearly defined boundary for both CT and MRI. These design decisions were successful at minimizing the image quality differences between the two image modalities.

The 4D-CT results in this study are comparable to the typical 4D-CT phantom studies in the literature. In a cross-institutional study, a commercial Quasar phantom was used in quality assurance of 4D-CT, where two targets with different sizes 15 mm diameter (1.77 ml) and 30 mm diameter (14.1 ml) were used. Given 1.5 and 2.5 cm motion for RR=10 and 20, their results showed that the volumetric detection errors in the single phase (mid-ventilation, end-inspiration and end-expiration), were 13.4 to 32.6% for small targets and 2.5 to 8.0% for large targets. In the current work, the size of the target is between these two extremes (23 mm diameter, 6.37 350 ml) and has a mean volumetric error of 5.2 to 10.3%. Based on the comparison with 4D-CT, the k-space self-gated 4D-MRI reported here (mean volumetric error 1.5 to 2.1%) achieves significantly superior performance in defining phase-resolved volumes (p=0.027). The respiratory rate (an index of target motion velocity) is an import factor for the image quality of 4D images. Our 4D-CT results show that phase-resolved geometric and volumetric deviations increase with an increase of motion velocity. At fast respiratory rates, 4D-CT is more likely to fail to accurately identify the target geometry for each individual phase. This is due to the limitation of the phase-sorting based 4D-CT reconstructions, which rely on the correlation between the external motion surrogate and the real target motion. Compared to 4D-CT, the image quality of 4D-MRI is relatively insensitive of target motion speed. In fact, the fast respiratory rate produces more self-gated signals in a given scanning time (8 minutes). Therefore, the image quality of 4D-MRI is not affected by motion speed. As shown in FIG. 4, all individual phases in 4D-MRI remain the same quality and nearly free of motion artifacts. Given this merit, target volumes measured at different phase and respiratory rates are all within 5% (FIG. 6(B)). The image quality for visual comparison also shows that 4D-MRI has excellent artifact resistance which is phase-independent and motion-independent.

Another factor that may introduce motion artifacts is irregular breathing patterns, which are commonly seen in patients. 4D-CT images are typically reconstructed based on retrospective sorting of sequential axial acquisitions of 3D-CTs using an external respiratory surrogate. Irregular breathing may induce position inconsistency in some slices which are not well correlated to the corrected respiratory phase during retrospective slice sorting. The phase-sorting errors may cause the correct phase image slice to be replaced by its nearby phase image slices. If the mis-sorting happens at the boundary of a structure (e.g., the target), an extra-boundary slice (target-stretching) or missing-boundary slice (target-squeezing) can be induced into the scanned target.

At present, no single 4D-CT scanning system can adequately handle irregular breathing. Several methods have been proposed to reduce this type of motion artifact, for example audio/video coaching and adapting the scan parameters to the breathing period. Similarly, irregular breathing would potentially pose challenges to retrospective slice sorting-based 4D-MRI techniques. Our 4D-MRI technique is designed to resist the respiratory irregularity. To reduce motion artifacts, the SG-labeled segment signals with abnormal time period or inconsistent position (≥mean±two standard deviations) are excluded from reconstruction. This strategy does not interfere with scanning process and avoids prospective gating which is usually vulnerable to irregular breathing patterns. Since the scan duration is a continuous 8-minute acquisition, the available data spanning the entire scan time is adequate to yield a quality phase reconstruction even with removal of some isolated data.

Conclusions

The recently developed self-gating-based k-space sorted 4D-MRI technique has been evaluated and compared with 4D-CT techniques using a MRI/CT compatible phantom. The 4D MRI technique provides a robust approach for accurately measuring phase-based target geometry while avoiding typical motion artifacts. Compared to 4D-CT, the current 4D-MRI technique demonstrates superior spatiotemporal resolution, and robust resistance to motion artifacts due to fast target motion and irregular breathing. The technique can be used extensively in abdominal targeting, motion gating, and toward implementing MRI-based adaptive radiotherapy.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A system comprising:
   (1) a phantom, comprising
      a target comprising a first gel with a first concentration of gadolinium (Gd);
      a target container comprising a second gel with a second concentration of Gd that is lower than the first concentration of Gd; and
      a water container comprising water with a Gd concentration of about $5 \times 10^{-6}$ Mol/mL to about $5 \times 10^{-5}$ Mol/mL; wherein the target is embedded within the target container and stabilized with the second gel, and the target container is contained within the water container;
   (2) a collapsible container operably connected to the phantom, such that inflation of the collapsible container causes the phantom to move;
   (3) a pump in fluid communication with the collapsible container; and
   (4) an electronic controller, wherein the electronic controller is configured to modulate pressure generated by the pump which in turn modulates the position of the phantom.

2. The system of claim 1, wherein the air pump is positioned in a separate room from the phantom.

3. The system of claim 1, wherein the target is spherical.

4. The system of claim 1, wherein the electronic controller comprises a controller module configured to allow the system to mimic human respiratory motion.

5. The system of claim 4, wherein the system is configured to simulate respiratory rates of 2-20 seconds per cycle and breathing depths of 3-30 mm.

6. The system of claim 1, further comprising an air intake port, wherein the air intake port is connected to and in fluid communication with the collapsible container.

7. The system of claim 6, wherein the air intake port comprises an air intake valve, and wherein the air intake valve is a one-way valve that only allows air to flow into the collapsible container.

8. The system of claim 7, further comprising a hose, wherein a first end of the hose connects to the air intake port and the second end of the hose connects to the air pump.

9. The system of claim 8, further comprising a linear actuator attached to an external surrogate, wherein the external surrogate comprises one or more markers, and wherein the linear actuator is attached to the phantom.

10. The system of claim 9, wherein one or more of the markers are infrared markers.

11. The system of claim 10, wherein the external surrogate is an RPM box.

12. The system of claim 9, wherein the linear actuator is in electronic communication with the electronic controller, and the electronic controller is configured to control the motion of the linear actuator.

13. The system of claim 12, wherein the electronic controller is an RSD controller.

14. The system of claim 1, further comprising a platform upon which the phantom rests.

15. The system of claim 14, wherein the platform comprises one or more wheels configured to allow the platform to roll.

16. The system of claim 15, further comprising a bed upon which the one or more wheels of the platform rest.

17. The system of claim 16, further comprising one or more tracks configured to accommodate the one or more wheels of the platform.

18. The system of claim 17, further comprising a magnetic resonance imaging scanner.

19. The system of claim 17 further comprising a computed tomography (CT) scanner.

20. The system of any of claim 1, wherein the collapsible air container is a bellow.

* * * * *